(12) United States Patent
Kaiser et al.

(10) Patent No.: US 11,684,532 B2
(45) Date of Patent: Jun. 27, 2023

(54) METHOD AND APPARATUS FOR SUPPORTING AND STABILIZING A PATIENT DURING HIP DISTRACTION

(71) Applicant: Stryker Corp., Kalamazoo, MI (US)

(72) Inventors: William Kaiser, Campbell, CA (US); Conrad Smith, Hollister, CA (US)

(73) Assignee: Stryker Corp., Kalamazoo, MI (US)

( * ) Notice: Subject to any disclaimer, the term of this patent is extended or adjusted under 35 U.S.C. 154(b) by 397 days.

(21) Appl. No.: 15/890,047

(22) Filed: Feb. 6, 2018

(65) Prior Publication Data

US 2018/0221229 A1   Aug. 9, 2018

Related U.S. Application Data

(60) Provisional application No. 62/546,600, filed on Aug. 17, 2017, provisional application No. 62/455,143, filed on Feb. 6, 2017.

(51) Int. Cl.
| | |
|---|---|
| *A61G 13/00* | (2006.01) |
| *A61B 17/02* | (2006.01) |
| *A61G 13/12* | (2006.01) |
| *A61F 5/37* | (2006.01) |
| *A61B 17/66* | (2006.01) |

(52) U.S. Cl.
CPC ........ *A61G 13/0081* (2016.11); *A61B 17/025* (2013.01); *A61G 13/126* (2013.01); *A61G 13/1245* (2013.01); *A61B 17/66* (2013.01); *A61B 2017/0268* (2013.01); *A61B 2017/0275* (2013.01); *A61F 5/37* (2013.01)

(58) Field of Classification Search
CPC ............ A61G 13/0081; A61G 13/1245; A61G 13/126; A61G 13/0036; A61G 13/123; A61G 13/125; A61G 13/101; A61G 13/04; A61G 13/08; A61G 13/0063; A61G 13/129; A61B 17/025; A61B 7/66; A61B 2017/0275; A61B 17/1764; A61B 2090/067; A61B 2017/0268; A61F 5/37; A61F 2/461; A61F 2002/4668; A61F 2/3859
See application file for complete search history.

(56) References Cited

U.S. PATENT DOCUMENTS

| | | |
|---|---|---|
| 2,150,314 A | 3/1939 | Bell |
| D130,079 S | 10/1941 | Weller |

(Continued)

FOREIGN PATENT DOCUMENTS

| | | |
|---|---|---|
| DE | 10 2005 023 477 | 11/2006 |
| DE | 20 2009 003 314 | 7/2009 |

(Continued)

OTHER PUBLICATIONS

Soule Medical, 2019, https://www.soulemedical.com.

(Continued)

*Primary Examiner* — Robert G Santos
*Assistant Examiner* — Adam C Ortiz
(74) *Attorney, Agent, or Firm* — Morrison & Foerster LLP

(57) ABSTRACT

A stabilizing pad configured for positioning on a surgical table onto which a patient is placed for a surgical procedure, the stabilizing pad comprising: a high friction top surface; and a high friction bottom surface; wherein the stabilizing pad comprises foam.

23 Claims, 24 Drawing Sheets

(56) References Cited

U.S. PATENT DOCUMENTS

| | | | |
|---|---|---|---|
| D171,677 S | 3/1954 | Adler | |
| 2,732,269 A | 4/1954 | Astroff | |
| 3,220,022 A | 11/1965 | Nelson | |
| D221,035 S | 6/1971 | Raines et al. | |
| 3,745,996 A | 7/1973 | Rush, Sr. | |
| 3,808,644 A | 5/1974 | Schoch | |
| D264,531 S | 5/1982 | Trade | |
| 4,539,763 A | 9/1985 | Walkhoff | |
| 4,551,932 A | 11/1985 | Schoch | |
| 4,573,482 A | 3/1986 | Williams, Jr. | |
| 4,708,510 A | 11/1987 | McConnell et al. | |
| 4,835,886 A | 6/1989 | Chemello et al. | |
| 4,841,650 A | 6/1989 | Dodge et al. | |
| 4,865,303 A * | 9/1989 | Hall | A61G 13/04 5/614 |
| 5,052,128 A | 10/1991 | Lonardo | |
| 5,162,039 A | 11/1992 | Dahners | |
| 5,177,882 A | 1/1993 | Berger | |
| 5,249,377 A | 10/1993 | Walkhoff | |
| 5,287,575 A | 2/1994 | Allen et al. | |
| 5,306,231 A | 4/1994 | Cullum et al. | |
| 5,560,577 A | 10/1996 | Keselman | |
| 5,582,379 A | 12/1996 | Keselman et al. | |
| 5,608,934 A | 3/1997 | Torrie et al. | |
| D385,040 S | 10/1997 | Keselman | |
| D387,581 S | 12/1997 | Parker et al. | |
| 5,702,389 A | 12/1997 | Taylor et al. | |
| D389,580 S | 1/1998 | Keselman et al. | |
| 5,728,095 A | 3/1998 | Taylor et al. | |
| 5,819,440 A | 10/1998 | Okajima | |
| 5,918,330 A | 7/1999 | Navarro et al. | |
| 5,971,984 A | 10/1999 | Taylor et al. | |
| 6,109,625 A | 8/2000 | Hewitt | |
| 6,162,223 A | 12/2000 | Orsak et al. | |
| 6,286,164 B1 | 9/2001 | Lamb et al. | |
| 6,678,908 B2 | 1/2004 | Borders et al. | |
| D546,599 S | 7/2007 | Goldberg | |
| 7,237,556 B2 | 7/2007 | Smothers et al. | |
| 7,337,483 B2 | 3/2008 | Boucher et al. | |
| 7,343,635 B2 | 3/2008 | Jackson | |
| 7,477,926 B2 | 1/2009 | McCombs | |
| 7,520,007 B2 | 4/2009 | Skripps | |
| 7,520,008 B2 | 4/2009 | Wong et al. | |
| 7,565,708 B2 | 7/2009 | Jackson | |
| 7,572,292 B2 | 8/2009 | Crabtree et al. | |
| 7,591,050 B2 | 9/2009 | Hammerslag | |
| 7,600,281 B2 | 10/2009 | Skripps | |
| 7,669,262 B2 | 3/2010 | Skripps et al. | |
| 7,677,249 B2 | 3/2010 | Kong et al. | |
| 7,739,762 B2 | 6/2010 | Lamb et al. | |
| RE41,412 E | 7/2010 | Van Steenburg | |
| 7,762,975 B2 | 7/2010 | Memminger | |
| 7,832,401 B2 | 11/2010 | Torrie et al. | |
| 7,862,570 B2 | 1/2011 | Russell et al. | |
| 7,878,992 B2 | 2/2011 | Mitsuishi et al. | |
| 7,882,583 B2 | 2/2011 | Skripps | |
| 7,947,006 B2 | 5/2011 | Torrie et al. | |
| 7,949,006 B2 | 5/2011 | Jagadesan et al. | |
| 7,949,386 B2 | 5/2011 | Buly et al. | |
| 7,979,932 B2 * | 7/2011 | Liang | A61G 13/08 5/613 |
| 8,011,045 B2 | 9/2011 | Skripps | |
| 8,037,884 B2 | 10/2011 | Weinstein et al. | |
| 8,055,487 B2 | 11/2011 | James | |
| 8,060,960 B2 | 11/2011 | Jackson | |
| 8,109,942 B2 | 2/2012 | Carson | |
| 8,152,816 B2 | 4/2012 | Tuma et al. | |
| D665,912 S | 8/2012 | Skripps | |
| 8,234,730 B2 | 8/2012 | Skripps | |
| 8,234,731 B2 | 8/2012 | Skripps | |
| 8,256,050 B2 | 9/2012 | Wong et al. | |
| 8,281,434 B2 | 10/2012 | Skripps | |
| 8,322,342 B2 | 12/2012 | Soto et al. | |
| 8,388,553 B2 | 3/2013 | James et al. | |
| 8,397,323 B2 | 3/2013 | Skripps et al. | |
| 8,413,660 B2 | 4/2013 | Weinstein et al. | |
| 8,464,720 B1 | 6/2013 | Pigazzi et al. | |
| 8,469,911 B2 | 6/2013 | Hiebert | |
| 8,486,070 B2 | 7/2013 | Morgan et al. | |
| 8,491,597 B2 | 7/2013 | Russell et al. | |
| 8,491,664 B2 | 7/2013 | McMahon et al. | |
| 8,511,314 B2 | 8/2013 | Pigazzi et al. | |
| 8,545,570 B2 | 10/2013 | Crabtree et al. | |
| 8,555,439 B2 | 10/2013 | Soto et al. | |
| 8,570,187 B2 | 10/2013 | Janna et al. | |
| 8,611,697 B2 | 12/2013 | Nathaniel et al. | |
| 8,679,187 B2 | 3/2014 | Allen et al. | |
| 8,690,806 B2 | 4/2014 | Hiebert | |
| 8,690,807 B2 | 4/2014 | Hiebert | |
| 8,702,712 B2 | 4/2014 | Jordan et al. | |
| 8,707,484 B2 | 4/2014 | Jackson et al. | |
| 8,707,486 B2 | 4/2014 | Chella et al. | |
| 8,719,979 B2 | 5/2014 | Jackson | |
| 8,721,643 B2 | 5/2014 | Morgan et al. | |
| 8,795,312 B2 | 8/2014 | Fan et al. | |
| 8,806,679 B2 | 8/2014 | Soto et al. | |
| 8,826,474 B2 | 9/2014 | Jackson | |
| 8,826,475 B2 | 9/2014 | Jackson | |
| 8,828,009 B2 | 9/2014 | Allen et al. | |
| 8,833,707 B2 | 9/2014 | Steinberg et al. | |
| 8,839,471 B2 | 9/2014 | Jackson | |
| 8,844,077 B2 | 9/2014 | Jackson et al. | |
| 8,845,568 B2 | 9/2014 | Clark et al. | |
| 8,856,986 B2 | 10/2014 | Jackson | |
| 8,890,511 B2 | 11/2014 | Belew | |
| 8,893,333 B2 | 11/2014 | Soto et al. | |
| 8,894,716 B2 | 11/2014 | McMahon et al. | |
| 8,938,826 B2 | 1/2015 | Jackson | |
| 8,944,065 B2 | 2/2015 | Slusarz, Jr. | |
| 8,945,026 B2 | 2/2015 | Moser et al. | |
| 8,978,180 B2 | 3/2015 | Jackson | |
| 8,986,228 B2 | 3/2015 | Auchinleck et al. | |
| 8,997,284 B2 | 4/2015 | Kreuzer et al. | |
| 8,997,286 B2 | 4/2015 | Wyslucha et al. | |
| 8,997,749 B2 | 4/2015 | Drake et al. | |
| 9,056,012 B2 | 6/2015 | Crabtree, Jr. et al. | |
| 9,072,646 B2 | 7/2015 | Skripps et al. | |
| 9,085,915 B1 | 7/2015 | Emmett | |
| 9,101,393 B2 | 8/2015 | Jordan et al. | |
| 9,107,792 B2 | 8/2015 | Catacchio et al. | |
| 9,119,610 B2 | 9/2015 | Matta et al. | |
| 9,161,875 B2 | 10/2015 | Clark et al. | |
| 9,161,876 B2 | 10/2015 | Pigazzi et al. | |
| 9,173,649 B2 | 11/2015 | Clark et al. | |
| 9,180,062 B2 | 11/2015 | Jackson | |
| 9,186,291 B2 | 11/2015 | Jackson et al. | |
| 9,198,817 B2 | 12/2015 | Jackson | |
| 9,205,013 B2 | 12/2015 | Jackson | |
| 9,211,223 B2 | 12/2015 | Jackson | |
| 9,226,865 B2 | 1/2016 | Jackson | |
| 9,233,043 B2 | 1/2016 | Labedz et al. | |
| 9,265,679 B2 | 2/2016 | Jackson | |
| 9,289,342 B2 | 3/2016 | Jackson | |
| 9,295,433 B2 | 3/2016 | Jackson et al. | |
| 9,295,556 B2 | 3/2016 | Perez, III et al. | |
| 9,301,897 B2 | 4/2016 | Jackson | |
| 9,308,145 B2 | 4/2016 | Jackson | |
| 9,364,380 B2 | 6/2016 | Jackson | |
| 9,456,945 B2 | 10/2016 | Jackson | |
| 9,468,576 B2 | 10/2016 | Jackson | |
| 9,510,987 B2 | 12/2016 | Jackson et al. | |
| 9,549,865 B2 | 1/2017 | Hiebert | |
| 9,610,206 B2 | 4/2017 | Jackson | |
| 9,672,662 B2 | 6/2017 | Scanlan et al. | |
| 9,750,656 B1 | 9/2017 | Pigazzi et al. | |
| 9,782,287 B2 | 10/2017 | Pigazzi et al. | |
| 9,931,262 B2 | 4/2018 | Pigazzi et al. | |
| 9,936,941 B2 | 4/2018 | Weisel et al. | |
| 9,949,883 B1 | 4/2018 | Pigazzi et al. | |
| 10,034,806 B1 | 7/2018 | Greenhalgh, Sr. | |
| D832,334 S | 10/2018 | Kushner et al. | |
| 10,130,542 B1 * | 11/2018 | Strawder | A61G 13/04 |
| 10,159,520 B2 | 12/2018 | Krickeberg et al. | |
| 10,828,218 B2 | 11/2020 | Shandas et al. | |

(56) References Cited

U.S. PATENT DOCUMENTS

| | | |
|---|---|---|
| 2002/0023298 A1 | 2/2002 | Lamb et al. |
| 2004/0003468 A1 | 1/2004 | Mitsuishi et al. |
| 2004/0092854 A1 | 5/2004 | D'Amico |
| 2004/0133979 A1 | 7/2004 | Newkirk et al. |
| 2004/0133983 A1 | 7/2004 | Newkirk et al. |
| 2005/0160533 A1 | 7/2005 | Boucher et al. |
| 2006/0047228 A1 | 3/2006 | Petelenz et al. |
| 2006/0074366 A1 | 4/2006 | Ryan et al. |
| 2006/0100562 A1 | 5/2006 | Pamplin |
| 2006/0130713 A1 | 6/2006 | Jones et al. |
| 2006/0185090 A1 | 8/2006 | Jackson |
| 2006/0271056 A1 | 11/2006 | Terrill-Grisoni et al. |
| 2007/0161935 A1 | 7/2007 | Torrie et al. |
| 2007/0251011 A1 | 11/2007 | Matta et al. |
| 2007/0277350 A1 | 12/2007 | Hines |
| 2008/0214976 A1 | 9/2008 | Memminger et al. |
| 2008/0216231 A1 | 9/2008 | Lambarth et al. |
| 2008/0309052 A1 | 12/2008 | Neiley et al. |
| 2009/0044339 A1* | 2/2009 | Morin .............. A61G 7/015 5/617 |
| 2011/0023893 A1 | 2/2011 | Striggow et al. |
| 2011/0119829 A1 | 5/2011 | Skripps et al. |
| 2011/0143898 A1* | 6/2011 | Trees ............ A63B 23/0405 482/142 |
| 2011/0190676 A1 | 8/2011 | Torrie et al. |
| 2012/0059376 A1 | 3/2012 | Rains et al. |
| 2012/0073476 A1 | 3/2012 | Lai |
| 2012/0204885 A1 | 8/2012 | Koch |
| 2012/0233782 A1 | 9/2012 | Kreuzer et al. |
| 2012/0240938 A1 | 9/2012 | Pamichev |
| 2012/0255122 A1 | 10/2012 | Diel et al. |
| 2012/0259261 A1 | 10/2012 | Clark et al. |
| 2012/0259343 A1 | 10/2012 | Clark et al. |
| 2012/0305005 A1 | 12/2012 | Keith-Lucas et al. |
| 2013/0081635 A1 | 4/2013 | Drake et al. |
| 2013/0111666 A1 | 5/2013 | Jackson |
| 2013/0133137 A1 | 5/2013 | Jackson et al. |
| 2013/0174853 A1 | 7/2013 | Pigazzi |
| 2013/0174854 A1 | 7/2013 | Pigazzi et al. |
| 2013/0191994 A1 | 8/2013 | Bellows et al. |
| 2013/0199541 A1 | 8/2013 | Sluss et al. |
| 2013/0247301 A1* | 9/2013 | Daley ............... A61G 13/101 5/613 |
| 2013/0269710 A1 | 10/2013 | Hight et al. |
| 2013/0312187 A1 | 11/2013 | Jackson |
| 2013/0312188 A1 | 11/2013 | Jackson |
| 2013/0318721 A1 | 12/2013 | Gauta |
| 2013/0338792 A1 | 12/2013 | Schmieding et al. |
| 2013/0345605 A1 | 12/2013 | Steele |
| 2014/0020181 A1 | 1/2014 | Jackson |
| 2014/0033434 A1 | 2/2014 | Jackson |
| 2014/0068863 A1 | 3/2014 | Clark et al. |
| 2014/0068866 A1 | 3/2014 | Catacchio et al. |
| 2014/0082842 A1 | 3/2014 | Jackson |
| 2014/0173827 A1 | 6/2014 | Hiebert |
| 2014/0174451 A1 | 6/2014 | Hiebert |
| 2014/0196212 A1 | 7/2014 | Jackson |
| 2014/0201913 A1 | 7/2014 | Jackson |
| 2014/0201914 A1 | 7/2014 | Jackson |
| 2014/0208512 A1 | 7/2014 | Jackson |
| 2014/0208513 A1 | 7/2014 | Hiebert |
| 2014/0215718 A1* | 8/2014 | Wootton ........... A61G 13/101 5/621 |
| 2014/0215855 A1 | 8/2014 | Frey |
| 2014/0222407 A1 | 8/2014 | Jordan et al. |
| 2014/0283845 A1 | 9/2014 | Slusarz, Jr. |
| 2014/0309646 A1 | 10/2014 | Fan et al. |
| 2014/0317847 A1 | 10/2014 | Jackson |
| 2014/0324056 A1 | 10/2014 | Nikolchev et al. |
| 2014/0352072 A1 | 12/2014 | Holladay |
| 2014/0359941 A1* | 12/2014 | Sharps ............... A61G 13/06 5/610 |
| 2014/0366271 A1 | 12/2014 | Marshall |
| 2015/0008201 A1 | 1/2015 | Qiang et al. |
| 2015/0032041 A1 | 1/2015 | Ingimundarson et al. |
| 2015/0059094 A1 | 3/2015 | Jackson |
| 2015/0067985 A1 | 3/2015 | Gaenzle |
| 2015/0088044 A1 | 3/2015 | Walborn et al. |
| 2015/0122268 A1 | 5/2015 | Slusarz, Jr. |
| 2015/0150743 A1 | 6/2015 | Jackson |
| 2015/0164724 A1 | 6/2015 | Drake et al. |
| 2015/0196447 A1 | 7/2015 | Henderson et al. |
| 2015/0202106 A1 | 7/2015 | Hight et al. |
| 2015/0231013 A1 | 8/2015 | Bernardoni et al. |
| 2015/0238273 A1 | 8/2015 | Jordan et al. |
| 2015/0238380 A1 | 8/2015 | Kreuzer et al. |
| 2015/0245915 A1 | 9/2015 | Crabtree, Jr. et al. |
| 2015/0245969 A1 | 9/2015 | Hight et al. |
| 2015/0245971 A1 | 9/2015 | Bernardoni et al. |
| 2015/0272611 A1 | 10/2015 | Skripps et al. |
| 2015/0290064 A1 | 10/2015 | Kreuzer et al. |
| 2015/0297435 A1 | 10/2015 | Visco |
| 2015/0342813 A1 | 12/2015 | Catacchio et al. |
| 2015/0366622 A1 | 12/2015 | Wyslucha et al. |
| 2016/0008201 A1 | 1/2016 | Jackson et al. |
| 2016/0038364 A1 | 2/2016 | Jackson |
| 2016/0051432 A1 | 2/2016 | Clark et al. |
| 2016/0067135 A1 | 3/2016 | Pigazzi et al. |
| 2016/0095784 A1 | 4/2016 | Catacchio et al. |
| 2016/0095785 A1 | 4/2016 | Catacchio et al. |
| 2016/0106612 A1 | 4/2016 | Clark et al. |
| 2016/0120720 A1 | 5/2016 | Hirsch |
| 2016/0120726 A1 | 5/2016 | Moriarty et al. |
| 2016/0184154 A1 | 6/2016 | Lafleche et al. |
| 2016/0228281 A1 | 8/2016 | Marshall et al. |
| 2016/0279007 A1 | 9/2016 | Flatt |
| 2016/0287461 A1* | 10/2016 | Naughton ........... A61G 13/101 |
| 2016/0317237 A1 | 11/2016 | Geiger |
| 2016/0338691 A1 | 11/2016 | Weber et al. |
| 2018/0140309 A1 | 5/2018 | Fouts et al. |
| 2018/0140493 A1 | 5/2018 | Shandas et al. |
| 2018/0221190 A1 | 8/2018 | Kaiser et al. |
| 2018/0221230 A1 | 8/2018 | Smith et al. |
| 2019/0091089 A1 | 3/2019 | Shandas et al. |
| 2022/0096304 A1 | 3/2022 | Kaiser et al. |

FOREIGN PATENT DOCUMENTS

| | | |
|---|---|---|
| DE | 20 2012 101 347 | 8/2012 |
| DE | 10 2011 016 456 | 2/2016 |
| EP | 2 574 325 | 4/2013 |
| EP | 2 623 082 | 8/2013 |
| EP | 2 618 313 | 7/2014 |
| EP | 2 873 405 | 5/2015 |
| EP | 2 982 880 | 2/2016 |
| EP | 2 802 305 | 10/2018 |
| WO | WO 03/061544 | 7/2003 |
| WO | WO 2006/091239 | 8/2006 |
| WO | WO 2007/021806 | 2/2007 |
| WO | WO 2007/080454 | 7/2007 |
| WO | WO 2008/150731 | 12/2008 |
| WO | WO 2009/062324 | 5/2009 |
| WO | WO 2013/034916 | 3/2013 |
| WO | 2013/106426 A2 | 7/2013 |
| WO | WO 2014/043538 | 3/2014 |
| WO | WO 2014/045194 | 3/2014 |
| WO | WO 2014/045199 | 3/2014 |
| WO | WO 2014/153329 | 9/2014 |
| WO | WO 2014/205218 | 12/2014 |
| WO | WO 2016/017479 | 2/2016 |
| WO | WO 2016/197142 | 12/2016 |

OTHER PUBLICATIONS

Steep Trendelenburg Positioners, Prime Medical LLC, 2019, http://primemedicalllc.com/steep-trendelenburg-positioners/.
Kollmorgen, Robert C., The Pink Hip Kit®: Postless Hip Arthroscopy Positioning System, Xodus Medical.
Pink Pad—Advanced Trendelenburg Positioning System, Xodus Medical Inc., 2018, https://www.xodusmedical.com/pinkpad.
The Pink Pad XL®: Advanced Trendelenburg Positioning System, Xodus Medical, 2018.

(56) References Cited

OTHER PUBLICATIONS

Hip Distraction System: Advanced solutions for supine hip arthroscopy procedures, Arthrex, 2013, pp. 1-6.

Mei-Dan, O. et al. Hip Arthroscopy Distraction Without the Use of Perineal Post: Prospective Study (Abstract), vol. 36, No. 1, Jan. 2013, pp. e1-e5.

Opfell, A., Hip Arthroscopy & Fracture Kit: Maximize patient safety during arthroscopic hip procedures, Xodus Medical, Jul. 12, 2018.

Terry, M.A., Arthroscopic Hip Patient Positioning Using the Advanced Supine Hip Positioning System: Hip Technique Guide, Smith & Nephew, 2013, pp. 1-8.

Harris, The Pink Hip Kit SN: Postless Positioning System—HIP40614SN, Xodus Medical, 2019.

Harris, The Pink Hip Kit SN: Postless Poitioning System—72205286, Xodus Medical, 2019, https://www.xodusmedical.com/Product/HIP40614SN.

Trendelenburg Positioning Kits, Soule Medical, 2018, https://www.soulemedical.com/index.php/trendelenburg-positioning-kit.

Young, D.A. et al., Technique allows for hip arthoscopy distraction without perineal post, Orthopedics Today, Jun. 2013, https://www.healio.com/orthopedics/arthroscopy/news/print/orthopedics-today/%7Bac540b4c-9b43-4736-ae8a-606b1457af8b%7D/technique-allows-for-hip-arthroscopy-distraction-without-perineal-post.

Hip Arthroscopy and Fracture Kit, SPK10246—Hip Arthroscopy and Fracture Kit with Perineal Post Cover.

"Hip Distraction System: Advanced solutions for supine hip arthroscopy procedures," technical brochure published by Arthrex, 2020; 6 pages.

"Secure and easy patient positioning," technical brochure published by Smith & Nephew, May 2015; 8 pages.

Communication pursuant to Article 94(3) EPC dated Mar. 12, 2020, directed to EP Application No. 16804665.4; 9 pages.

International Search Report and Written Opinion dated Apr. 13, 2018, directed to International PCT/US2018/017099; 9 pages.

International Search Report and Written Opinion dated Aug. 13, 2016, directed to International Application No. PCT/US2016/036090; 8 pages.

International Search Report and Written Opinion dated May 30, 2018, directed to International Application No. PCT/US2018/017088; 13 pages.

Merriam-Webster, "outrigger," https://www.merriam-webster.com/dictionary/outrigger, retrieved on Sep. 9, 2020; 1 page.

Search Report dated Nov. 3, 2020, directed to EP Application No. 18747404.4; 6 pages.

Shandas et al., U.S. Office Action dated Feb. 10, 2021, directed to U.S. Appl. No. 15/579,409; 13 pages.

Shandas et al., U.S. Office Action dated Sep. 8, 2020, directed to U.S. Appl. No. 15/579,409; 8 pages.

Smith et al., U.S. Office Action dated Mar. 22, 2021 directed to U.S. Appl. No. 15/890,124; 39 pages.

Smith et al., U.S. Office Action dated Sep. 16, 2020, directed to U.S. Appl. No. 15/890,124; 29 pages.

Extended Search Report dated Feb. 10, 2021, directed to EP Application No. 18747256.8; 10 pages.

Shandas et al., U.S. Notice of Allowance and Fee(s) Due dated Feb. 10, 2020, directed to U.S. Appl. No. 16/728,876; 10 pages.

Shandas et al., U.S. Notice of Allowance and Fee(s) Due dated Jul. 1, 2020, directed to U.S. Appl. No. 16/728,876; 8 pages.

Shandas et al., U.S. Office Action dated Jul. 8, 2021, directed to U.S. Appl. No. 15/579,409; 11 pages.

Shandas et al., U.S. Office Action dated Apr. 26, 2019, directed to U.S. Appl. No. 16/197,913; 17 pages.

Shandas et al., U.S. Office Action dated Oct. 7, 2019, directed to U.S. Appl. No. 16/197,913; 17 pages.

Smith et al., U.S. Advisory Action dated Jun. 28, 2021, directed to U.S. Appl. No. 15/890,124; 4 pages.

Kaiser et al., U.S. Appl. No. 62/954,888, filed Dec. 30, 2019, for "Apparatus and Method for Patient Positioning" [A copy is not submitted herewith pursuant to the waiver of 37 C.F.R. § 1.98(a)(2)(iii) issued by the Office on Sep. 21, 2004.].

Klauschie et al. (Jul./Aug. 2010). "Use of Anti-Skid Material and Patient-Positioning To Prevent Patient Shifting during Robotic-Assisted Gynecologic Procedures," The Journal of Minimally Invasive Gynecology 17(4):504-507.

Shandas et al., U.S. Advisory Action dated May 19, 2021, directed to U.S. Appl. No. 15/579,409; 3 pages.

Shandas et al., U.S. Restriction Requirement dated May 13, 2020, directed to U.S. Appl. No. 15/579,409; 8 pages.

Smith et al., U.S. Election Requirement dated Mar. 17, 2020, directed to U.S. Appl. No. 15/890,124; 7 pages.

U.S. Surgitech, Inc. (Mar. 2019). "SurgyPad—A Unique & Revolutionary Patient Positioning System" Brochure; 1 page.

Xodus Medical. (Aug. 2019) "Maximizing Trendelenburg Safety—Advanced Trendelenburg Patient Positioning System," located at https://xodusmedical.com/ProductCategory/Trendelenburg; 14 pages.

Extended European Search Report dated Jan. 7, 2019, directed to EP Application No. 16804665.4; 8 pages.

Kaiser et al., U.S. Notice of Allowance and Fee(s) Due dated Sep. 15, 2022, directed to U.S. Appl. No. 17/488,213; 9 pages.

Mei-Dan et al. (Mar. 2018). "Hip Distraction Without a Perineal Post: A Prospective Study of 1000 Hip Arthroscopy Cases," The American Journal of Sports Medicine 46(3):632-641.

Office Action dated Dec. 23, 2021, directed to EP Application No. 16 804 665.4; 5 pages.

Office Action dated Jul. 5, 2022, directed to EP Application No. 18 747 256.8; 4 pages.

Shandas et al., U.S. Notice of Allowance and Fee(s) Due dated Feb. 16, 2022, directed to U.S. Appl. No. 15/579,409; 10 pages.

Smith et al., U.S. Notice of Allowance and Fee(s) Due dated Apr. 26, 2022, directed to U.S. Appl. No. 15/890,124; 10 pages.

* cited by examiner

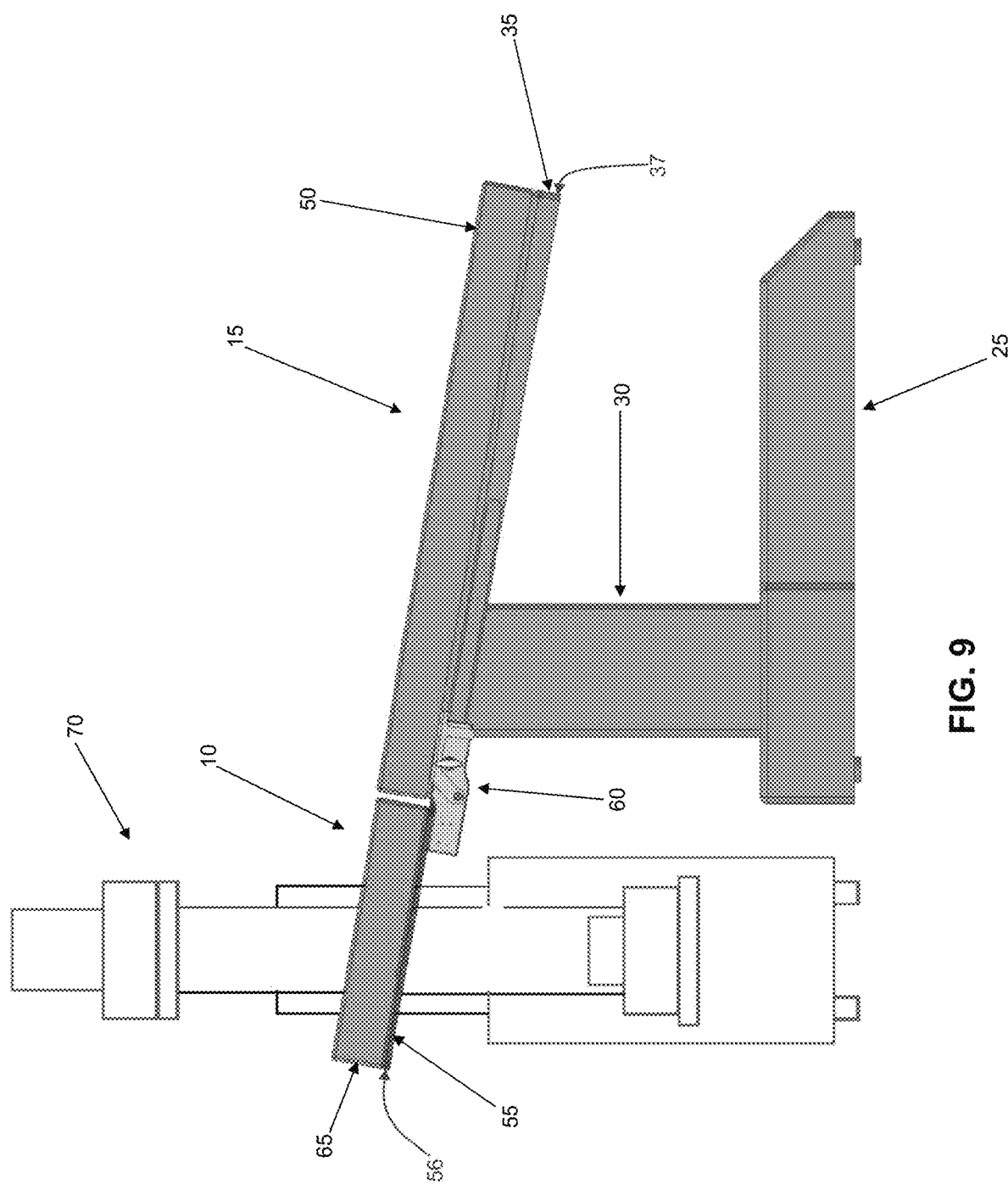

METHOD AND APPARATUS FOR SUPPORTING AND STABILIZING A PATIENT DURING HIP DISTRACTION

REFERENCE TO PENDING PRIOR PATENT APPLICATIONS

This patent application claims benefit of:

(i) pending prior U.S. Provisional Patent Application Ser. No. 62/455,143, filed Feb. 6, 2017 by Stryker Corp. and William Kaiser et al. for METHOD AND APPARATUS FOR POSITIONING AND STABILIZING A PATIENT DURING HIP DISTRACTION; and (ii) pending prior U.S. Provisional Patent Application Ser. No. 62/546,600, filed Aug. 17, 2017 by Stryker Corp. and William Kaiser et al. for METHOD AND APPARATUS FOR SUPPORTING AND STABILIZING A PATIENT DURING HIP DISTRACTION.

The two (2) above-identified patent applications are hereby incorporated herein by reference.

FIELD OF THE INVENTION

This invention relates to medical apparatus in general, and more particularly to medical apparatus for supporting and stabilizing a patient during hip distraction.

BACKGROUND OF THE INVENTION

When performing surgical procedures on the hip joint, it is common to distract the hip joint prior to the surgery in order to provide additional room within the hip joint during the surgery and in order to better present selected anatomy to the surgeon during the surgery. This hip distraction is commonly achieved by applying a distraction force to the distal end of the leg of the patient. Currently, a surgical boot is placed on the foot and lower leg of the patient, the surgical boot is connected to a distraction frame, and then the distraction frame is used to apply a distraction force to the surgical boot, whereby to apply a distraction force to the leg of the patient.

With conventional hip distraction, it is common to provide a padded post between the legs of the patient. This padded post provides a counterforce to the anatomy when the distraction force is applied to the surgical boot. However, the use of a padded post can create complications, since the padded post can press against the pudendal nerve of the patient, and/or the sciatic nerve of the patient, during distraction. Additionally, the padded post can exert pressure on the blood vessels in the leg of the patient during distraction. Thus, it would be desirable to minimize or eliminate the use of the padded post if other means could be used to provide a counterforce to the anatomy when the distraction force is applied to the surgical boot.

In addition to the foregoing, during many surgeries involving hip distraction, it can be desirable to image the anatomy which is being operated on using X-ray and/or CT imaging. However, conventional surgical tables are typically made out of radiopaque materials, thereby making it difficult or impossible to image the anatomy which is being operated on using these imaging modalities while the anatomy is supported on a conventional surgical table. As a result, it is frequently necessary to suspend the anatomy which is being operated on off one end of the surgical table so that the anatomy which is being operated on can be imaged using X-ray and/or CT imaging. This can significantly complicate and/or impede the surgery. Alternatively, it may be necessary to forego the use of X-ray and/or CT imaging during the surgery. Thus it would be desirable to provide a support for receiving and supporting the anatomy of a patient without significantly interfering with X-ray or CT imaging.

With some surgeries, it can be desirable to position the patient in the so-called "Trendelenburg position", e.g., during abdominal surgery. When disposed in the Trendelenburg position, the patient lies on the surgical table "flat on their back", with their feet higher than their head, e.g., by approximately 15-30 degrees. In order to facilitate this arrangement, the surgical table is typically tilted so that the patient's head is angled downward and the patient's feet are angled upward.

In the case of hip arthroscopy, it has been recognized that positioning the patient in this manner can facilitate distraction of the hip joint without a perineal post; that is, the gravitational weight of the patient inclined in the Trendelenburg position counteracts the distraction force in lieu of the perineal post. The frictional forces of the patient on the surgical table also contribute to counteract the distraction force. This approach has sometimes been referred to as "post-less" hip arthroscopy.

Numerous benefits are achieved by practicing post-less hip distraction.

One benefit of post-less hip distraction is that there is no post to press against the pudendal nerve of the patient, and/or the sciatic nerve of the patient, and/or the blood vessels of the patient, during distraction.

Another benefit of post-less hip distraction is that the non-operative leg remains relaxed while the operative leg is being "pulled on" for distraction. This is because gravity and the friction associated with the tilted surgical table are being used to keep the patient stable on the surgical table, not a post mounted to the surgical table. A post acts as a point of counter-traction; as such, the hip pivots around the post, resulting in a transfer of force to the non-operative leg. Without a post, there is no fulcrum and hence no force is transferred to the non-operative leg. This can benefit the patient inasmuch as any possible risks associated with forces being applied to the non-operative leg (such as neurovascular damage) are eliminated.

Another benefit of post-less hip distraction is that a post-less procedure results in less pelvic tilt than conventional distraction using a post. Again, because the post acts as a point of counter-traction, it imparts a force on the perineum of the patient, and can act as a fulcrum. For example, in the frontal plane, the pelvis can rotate around the post. This can result in pelvic tilt, which can be problematic.

In addition to the foregoing, in a typical hip arthroscopy procedure, distraction is used for central compartment work while peripheral compartment work is typically done "off-traction" (i.e., without a distraction force being applied to the leg of the patient). In a post-less procedure, the surgical table may be inclined for the portion of the procedure which requires traction (i.e., while work is done in the central compartment), but the surgical table can either be inclined or flat during the portion of the procedure which does not require traction (i.e., while work is done in the peripheral compartment). This can provide benefits to the surgeon.

In some hip arthroscopy procedures, the post may be removed when traction is not required, such as while work is being done in the peripheral compartment of the hip. However, there are times when it may be necessary to re-introduce the post (such as when traction is needed to check on work done in the central compartment, or when a bilateral procedure is performed and traction is needed for the other hip). However, it can be cumbersome and difficult to re-mount the post to the surgical table while keeping the sterile drape in place. In fact, the user must crawl under the drape and re-mount the post to the surgical table without having much visibility. Care must also be taken to avoid entrapment of the patient's anatomy (e.g., the genitalia) during the re-mounting of the post to the surgical table, which can be difficult to do and which can carry significant risk for the patient. In a post-less procedure, there is no post to manage.

Thus it will be appreciated that numerous advantages can be obtained using post-less hip distraction.

It should also be appreciated that, even if a post is used, advantages can be obtained if the patient can be positioned so as to minimize the forces applied to the patient via the post. By way of example but not limitation, even if a post is used, positioning the patient in the Trendelenburg position can minimize the forces applied to the patient via the post. In other words, performing a post-less hip arthroscopy has all of the aforementioned benefits, however, in certain circumstances, it may still be required or beneficial to use a post. But even in the instances where a post may be required or beneficial, the forces applied to the patient via the post can be diminished through the use of Trendelenburg positioning.

When the patient is disposed in the Trendelenburg position, gravity acts to pull the patient downward, towards their head, and the body of the patient could slide on the surgical table. Additionally, during post-less hip distraction, the patient could slide on the surgical table when force is applied to the patient's leg in order to effect the hip distraction. For example, the patient could slide distally (i.e., towards their feet) as the leg is pulled distally by the distraction frame. The patient could also slide or roll laterally towards the side edge of the surgical table, e.g., this could be the result of the leg being abducted when the pulling force is applied to the distal end of the leg, thereby generating a lateral force in addition to the distal force. Such unintended movement of the patient's body can disrupt the surgical procedure and/or cause tissue damage. In extreme cases, the patient could even fall off of the surgical table.

The present invention is intended to provide new and improved approaches for supporting and stabilizing a patient during hip distraction, both with and without a post. Such approaches are intended to provide improved hip distraction, facilitate post-less hip distraction, minimize pressure on a patient if a post is used, and prevent a patient from sliding or rolling on the surgical table during hip distraction.

SUMMARY OF THE INVENTION

The present invention provides new and improved approaches for transferring, supporting and stabilizing a patient during hip distraction. Such approaches are intended to provide improved hip distraction, facilitate post-less hip distraction, minimize pressure on a patient if a post is used, and prevent a patient from sliding or rolling on the surgical table during hip distraction.

More particularly, the present invention comprises the provision and use of a novel system for transferring, supporting and stabilizing a patient during hip distraction.

In one preferred form of the invention, there is provided a novel system for transferring, supporting and stabilizing a patient during hip distraction. The novel system generally comprises a table extender for mounting to one end of a surgical table, a stabilizing pad for positioning on the surgical table and the table extender so that the patient resides on the stabilizing pad, and a patient strap for securing the patient to the surgical table. Additionally, the novel system may also comprise a transfer sheet and/or a leg support.

In one form of the invention, there is provided a stabilizing pad configured for positioning on a surgical table onto which a patient is placed for a surgical procedure, the stabilizing pad comprising:

a high friction top surface; and a high friction bottom surface;

wherein the stabilizing pad comprises foam.

In another form of the invention, there is provided a stabilizing pad configured for positioning on a surgical table onto which a patient is placed for a surgical procedure, the stabilizing pad comprising a raised portion extending laterally across the width of the stabilizing pad.

In another form of the invention, there is provided a table extender, the table extender comprising:

a proximal portion configured for attachment to a surgical table;

a distal portion disposed opposite the proximal portion; and an intermediate portion disposed between the proximal portion and the distal portion, wherein the distal portion of the table extender and the intermediate portion of the table extender are substantially completely radiolucent.

In another form of the invention, there is provided a method for positioning a patient for surgery, the method comprising:

providing a surgical table and a table extender mounted to the surgical table, wherein at least a middle portion of the table extender is radiolucent; and positioning the patient on the surgical table and the table extender so that the patient's hip joints are located between approximately ⅓ to approximately ⅔ of the distance along the length of the table extender.

In another form of the invention, there is provided a method for positioning a patient for surgery, the method comprising:

providing a surgical table;

positioning a leg support adjacent to the distal end of the surgical table;

positioning the patient on the surgical table approximately in the position the patient is to occupy during surgery, with the legs of the patient supported on the leg support;

supporting the distal ends of the patient's legs with a distraction frame; and removing the leg support from its position adjacent to the distal end of the surgical table.

In another form of the invention, there is provided a method for positioning a patient for surgery, the method comprising:

providing a surgical table;

providing a stabilizing pad disposed on the surgical table at the location that the patient is to occupy during surgery, wherein the stabilizing pad has a high coefficient of friction;

placing the patient on a transfer sheet located on at least a portion of the stabilizing pad which is disposed on the surgical table in a position cephalad to the position the patient is to occupy during surgery, wherein the transfer sheet has a low coefficient of friction;

sliding the patient and the transfer sheet in a caudal direction on the stabilizing pad so that the patient is in the position the patient is to occupy during surgery; and removing the transfer sheet.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 5-9, 9A and 9B are schematic views showing further details of the table extender of the novel system shown in FIGS. 1-4;

DETAILED DESCRIPTION OF THE PREFERRED EMBODIMENTS

The present invention provides new and improved approaches for transferring, supporting and stabilizing a patient during hip distraction. Such approaches are intended to provide improved hip distraction, facilitate post-less hip distraction, minimize pressure on a patient if a post is used, and prevent a patient from sliding or rolling on the surgical table during hip distraction.

More particularly, the present invention comprises the provision and use of a novel system for transferring, supporting and stabilizing a patient during hip distraction.

The Novel System in General

Figure 1:
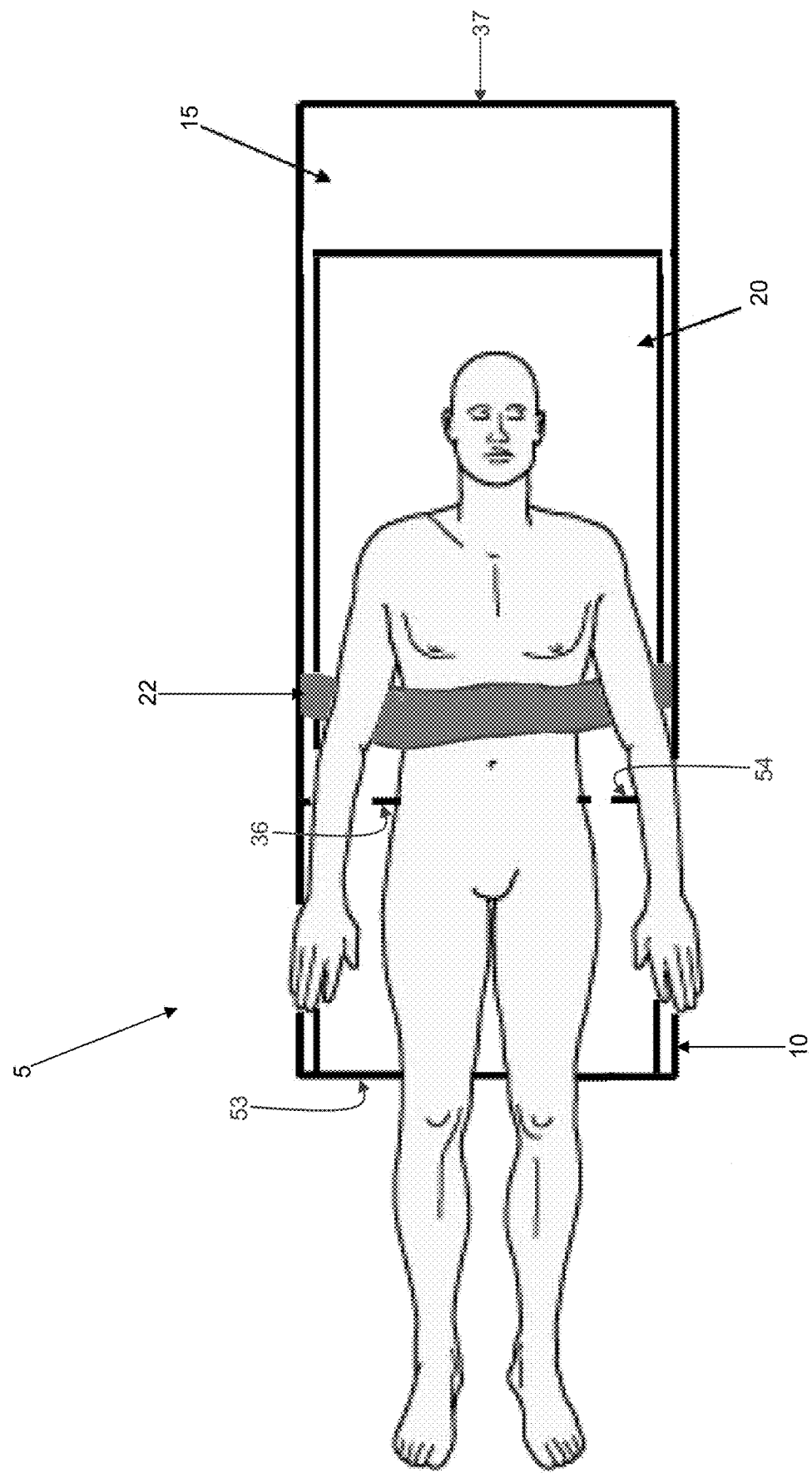
FIGS. 1-4 are schematic views showing one preferred form of the novel system for supporting and stabilizing a patient during hip distraction.
Figure 2:
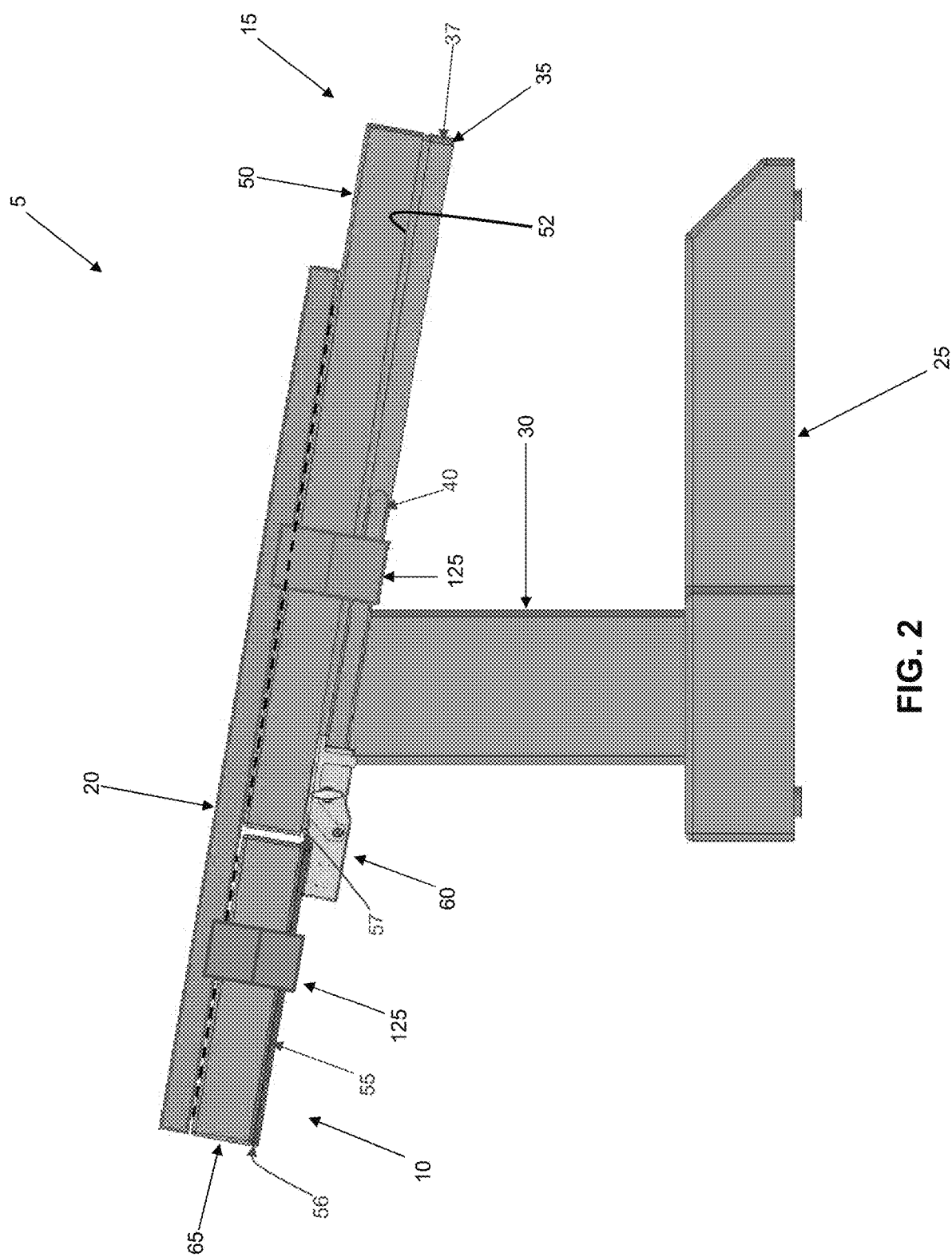
Figure 3:
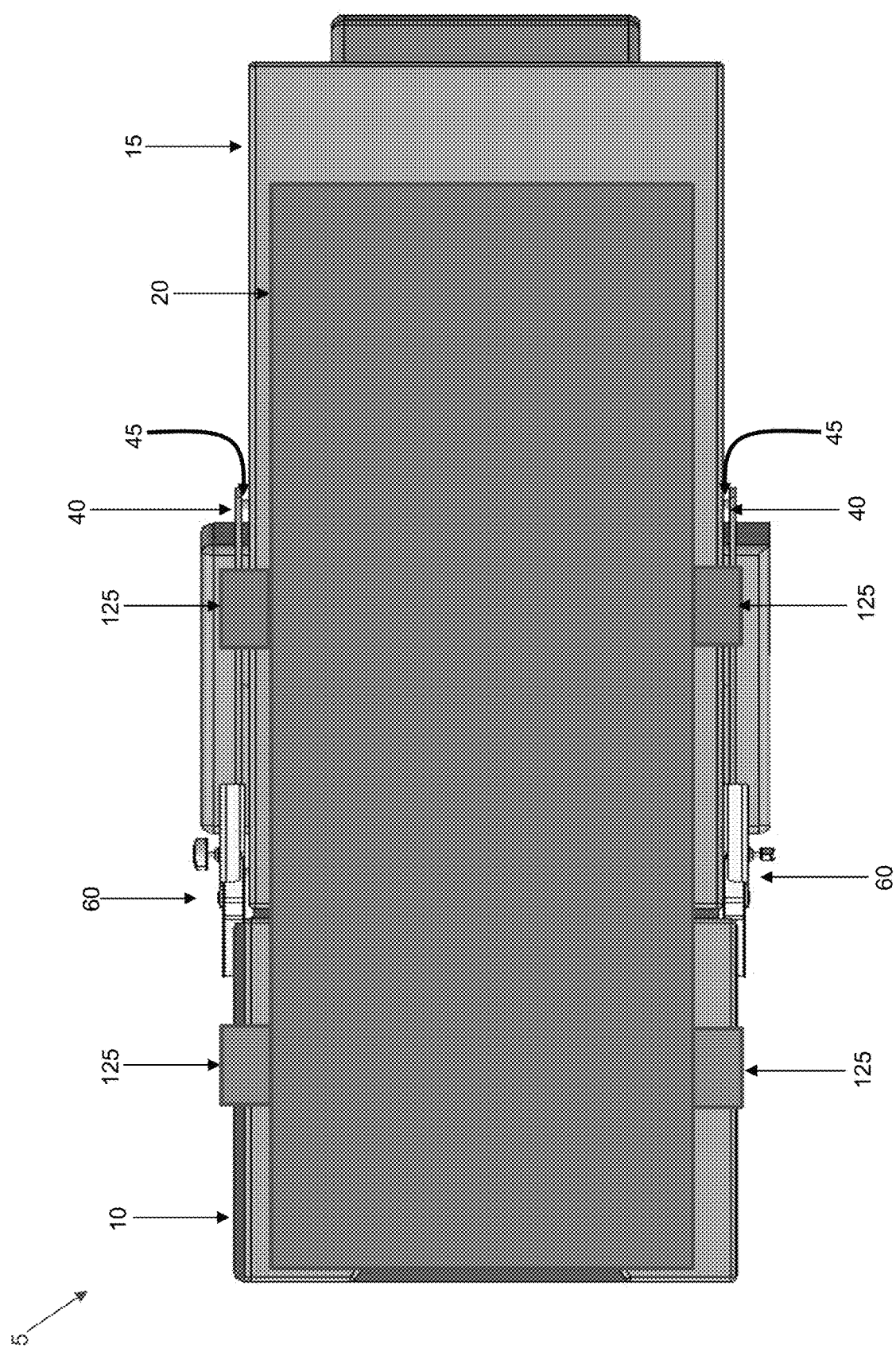
Figure 4:
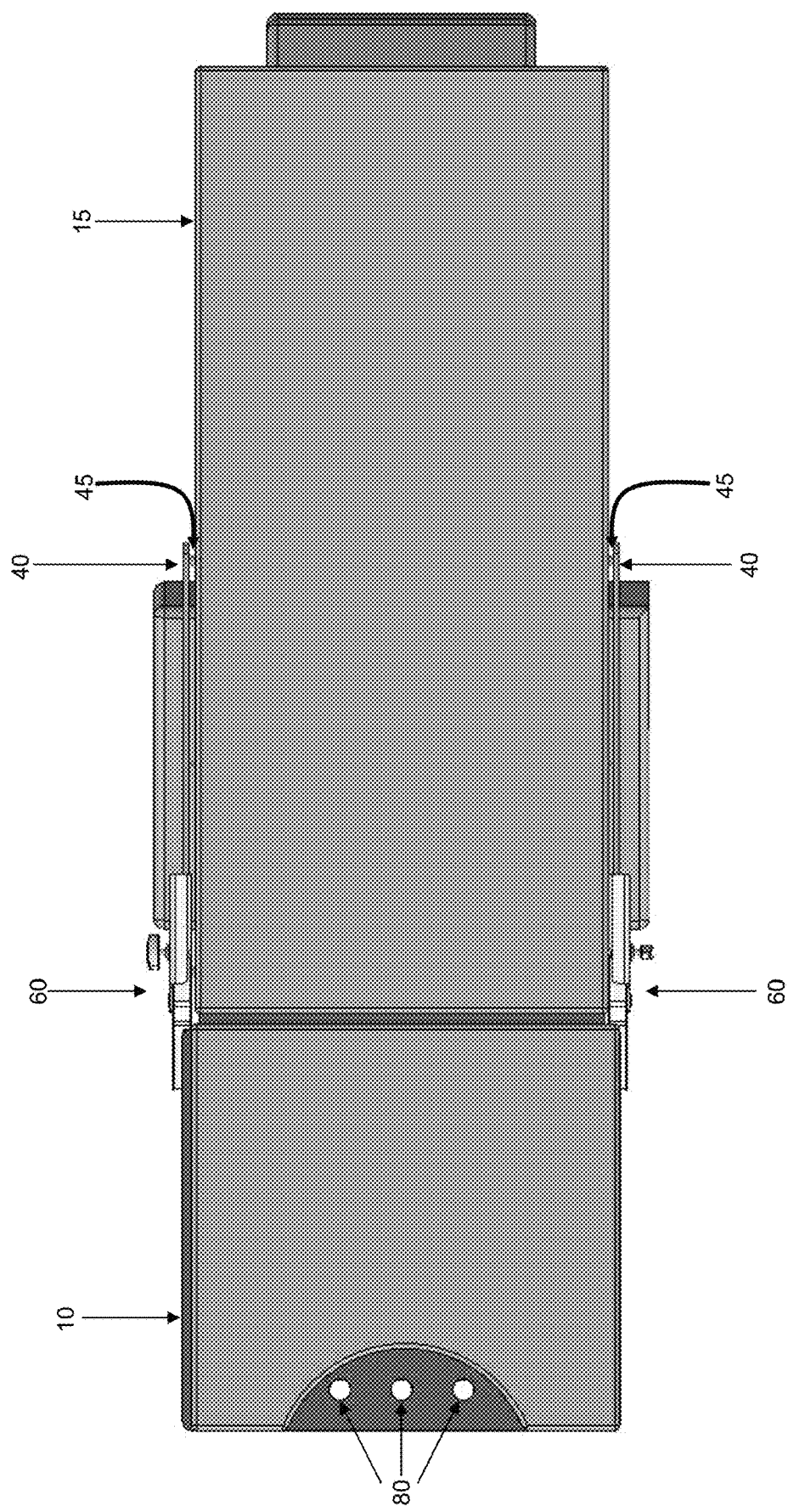
Figure 5:
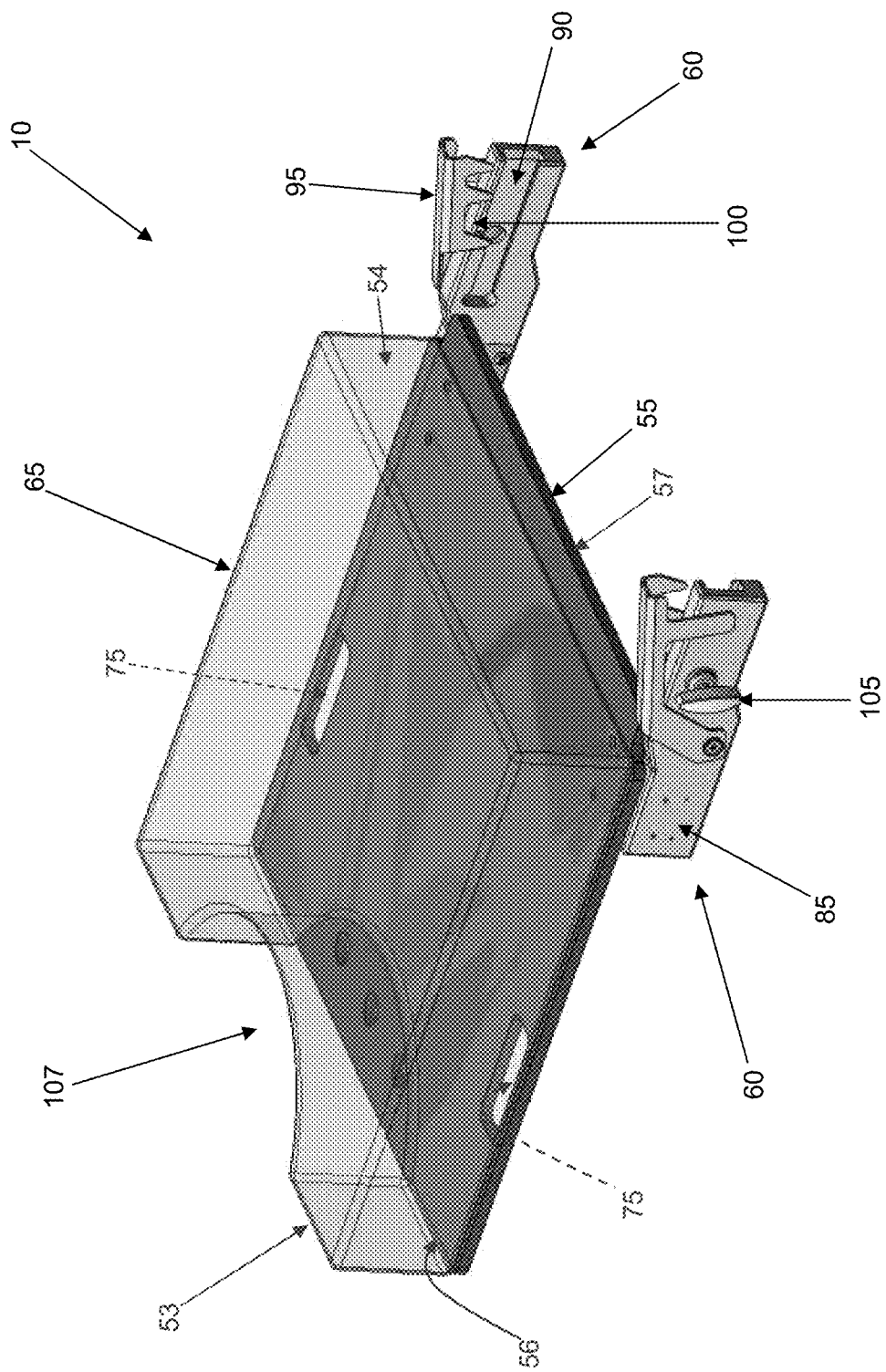
Figure 6:
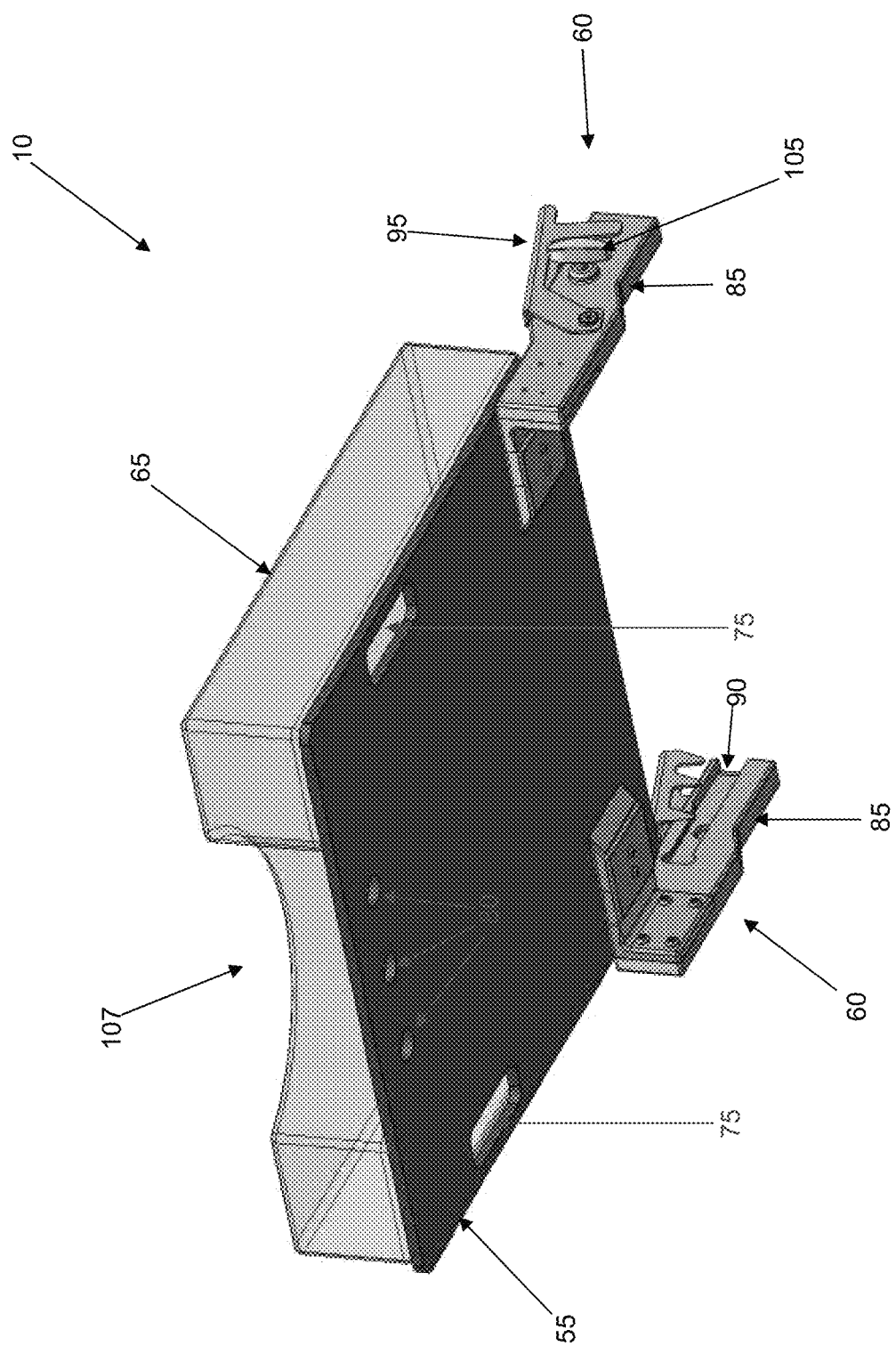
Figure 7:
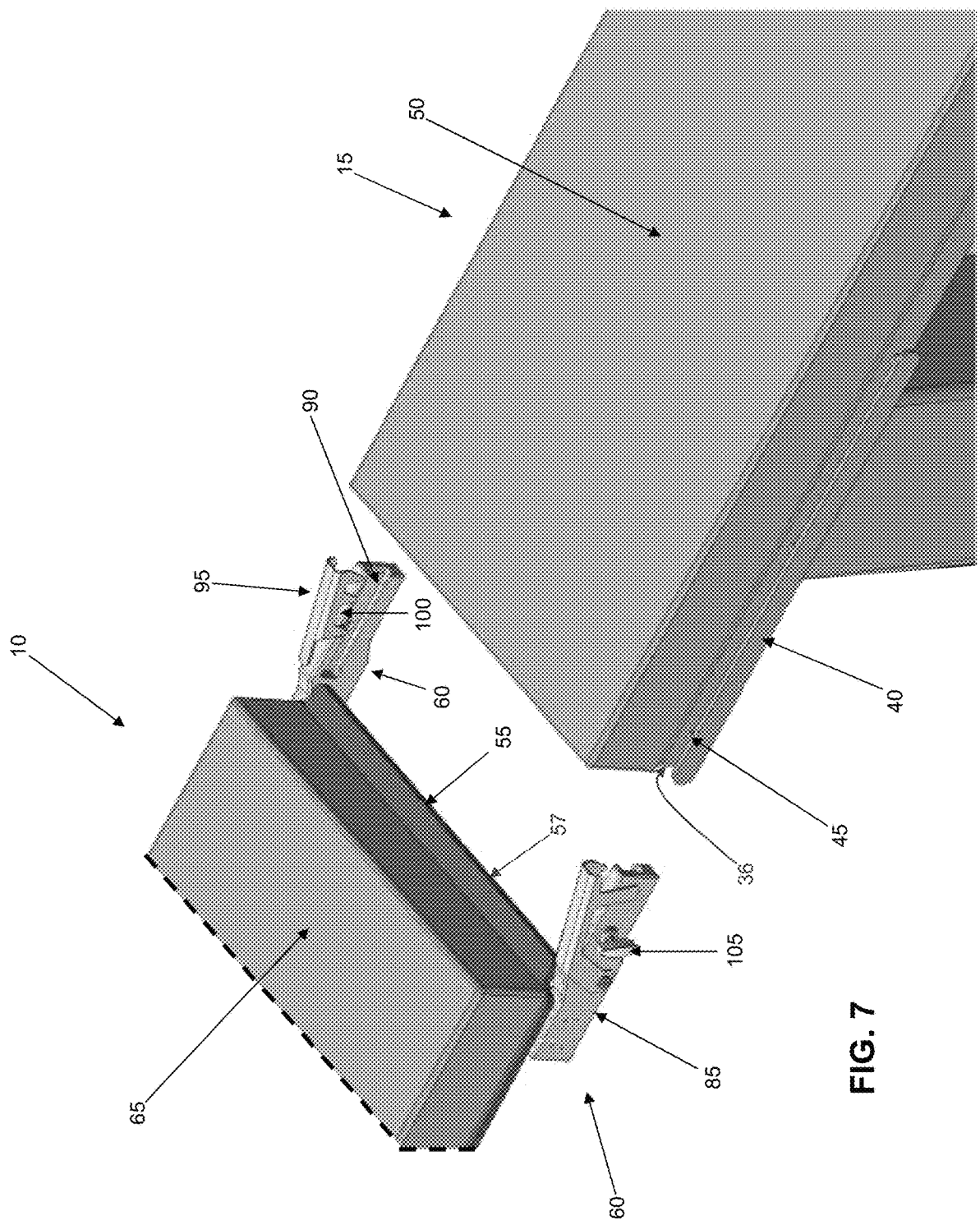
Figure 8:
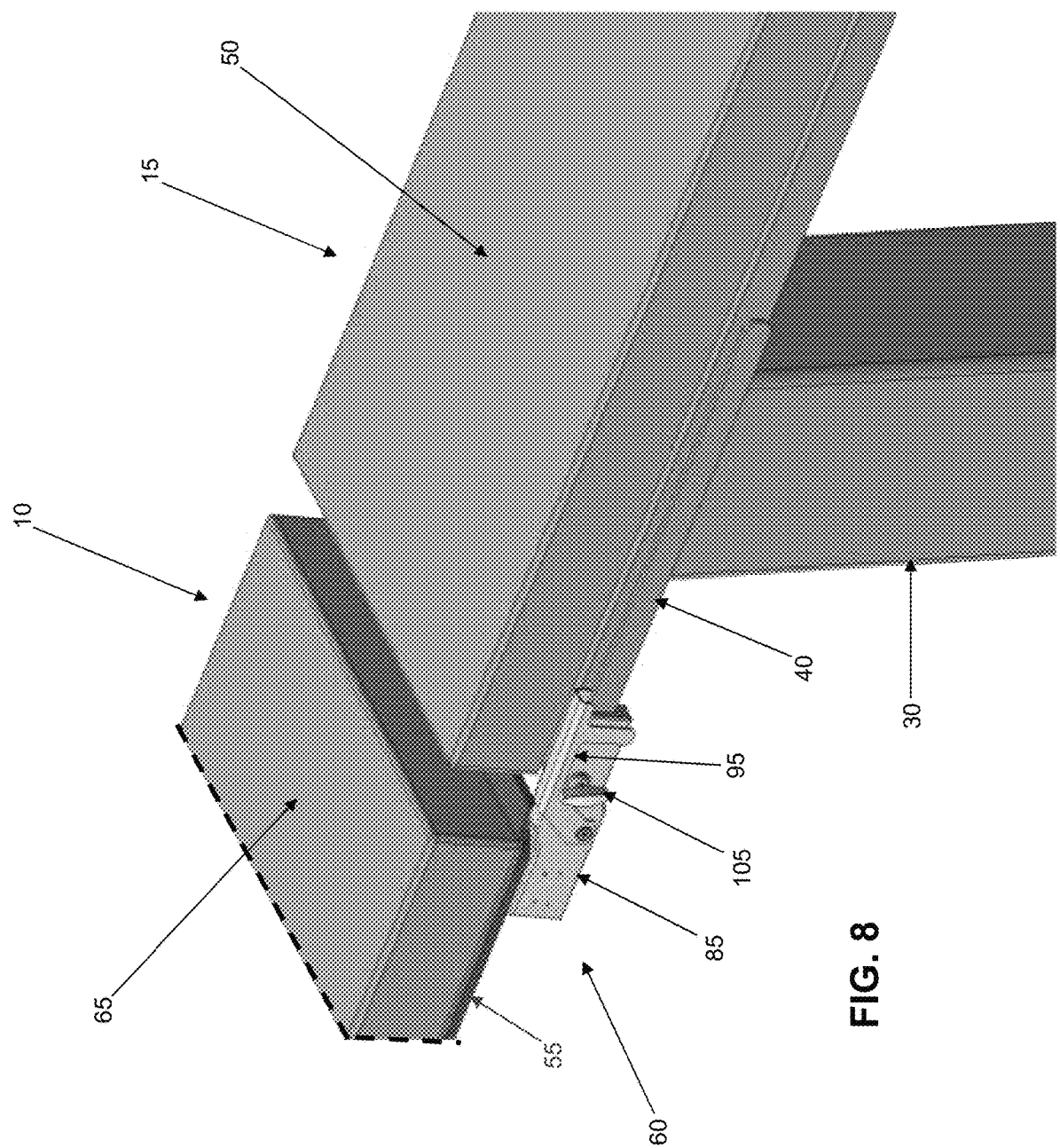
Figure 9A:
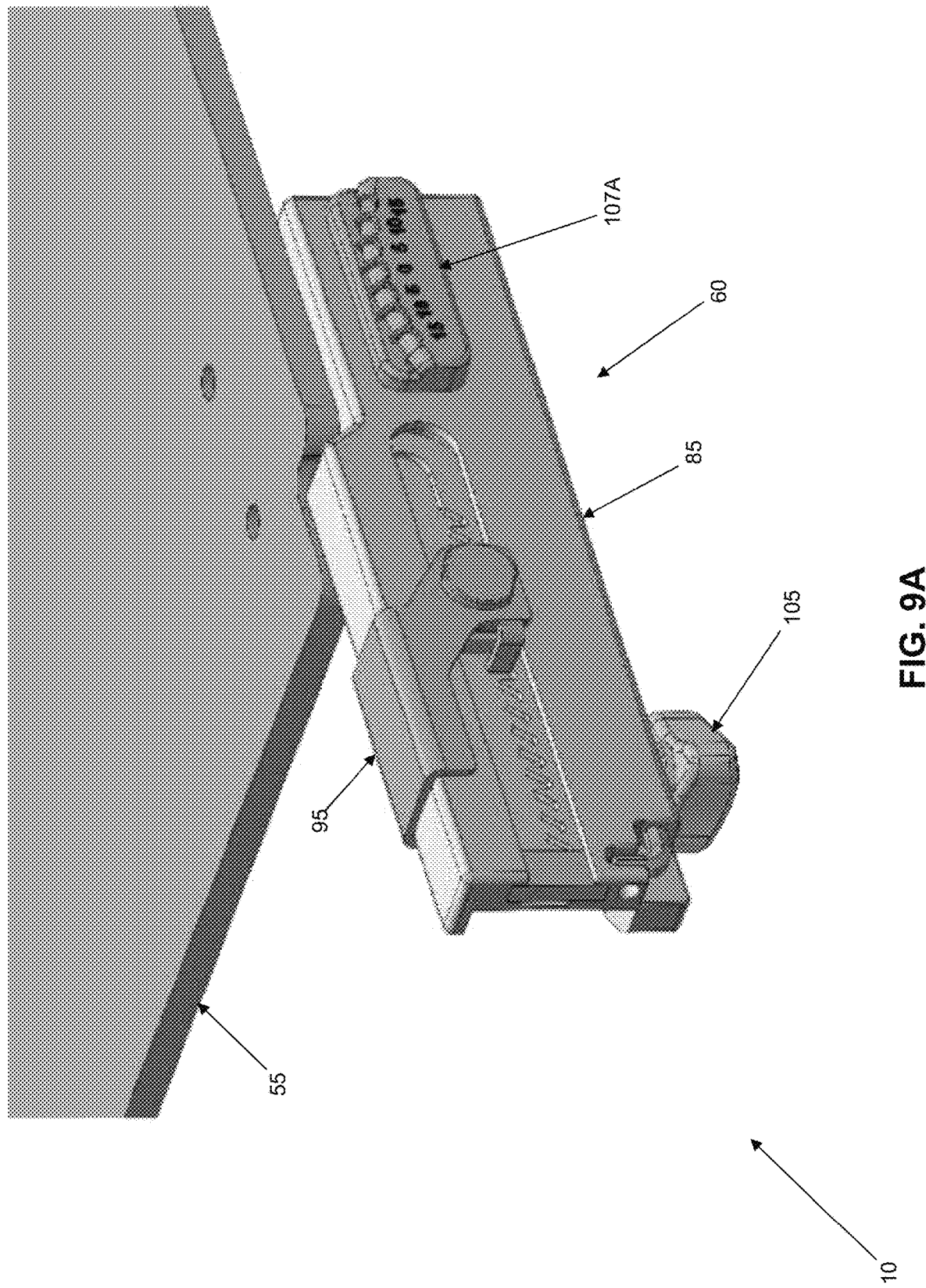
Figure 9B:
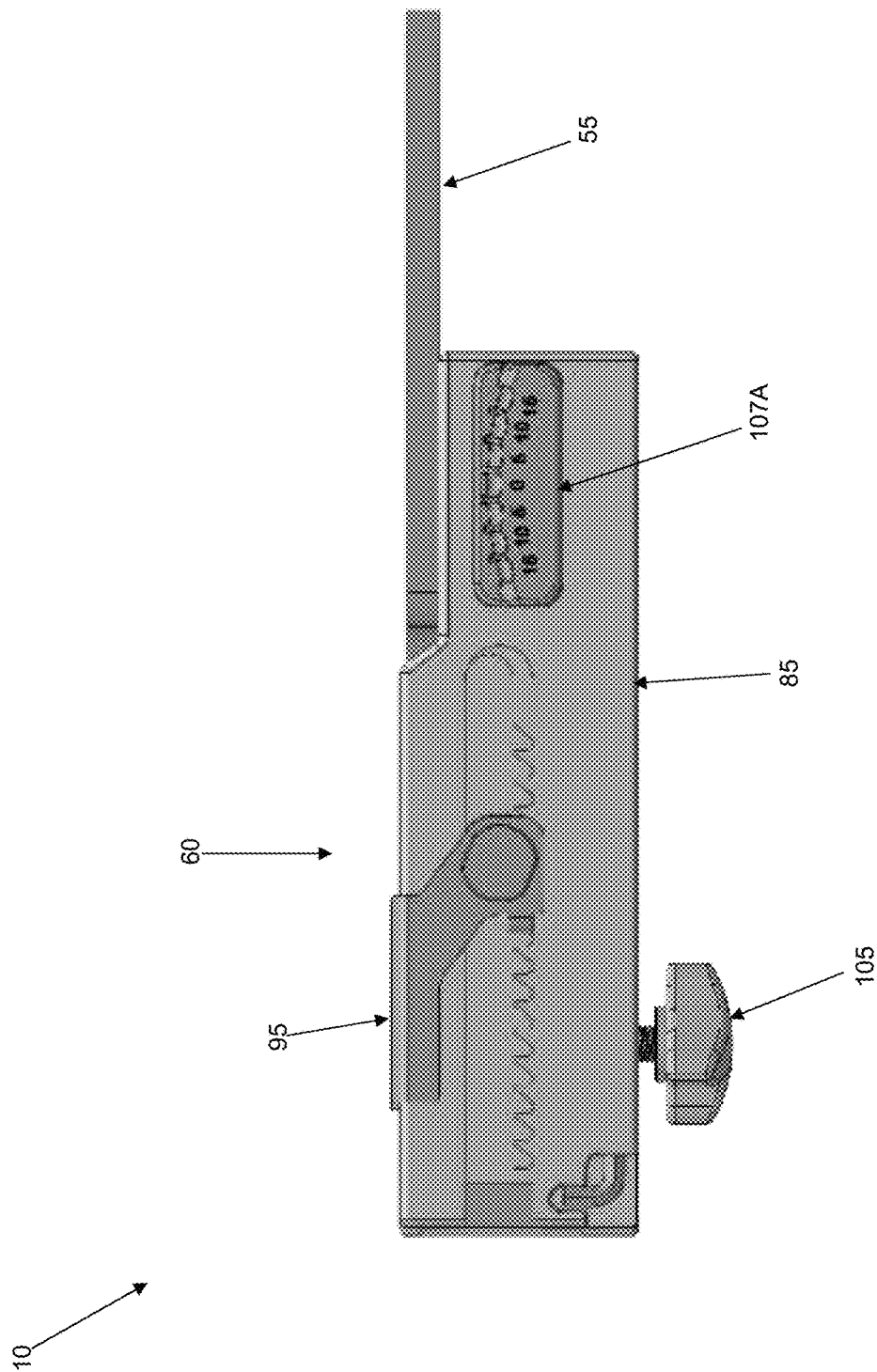

In one preferred form of the invention, and looking now at FIGS. 1-3, there is provided a novel system 5 for transferring, supporting and stabilizing a patient during hip distraction. Novel system 5 is intended to provide improved hip distraction, facilitate post-less hip distraction, minimize pressure on a patient if a post is used, and prevent a patient from sliding or rolling on the surgical table during hip distraction.

Novel system 5 generally comprises a table extender 10 for mounting to one end of a surgical table 15, a stabilizing pad 20 for positioning on surgical table 15 and table extender 10 so that the patient resides on stabilizing pad 20, and a patient strap 22 for securing the patient to surgical table 15.

Table Extender 10

Still looking now at FIGS. 1-3, surgical table 15 is a conventional surgical table of the sort well known in the art. Surgical table 15 typically comprises a base 25 for contacting the operating room floor, a pedestal 30 rising from base 25, and a platform 35 for supporting the patient. Platform 35 generally comprises a distal end 36 and a proximal end 37. Platform 35 can generally be tilted in a longitudinal and/or lateral direction relative to pedestal 30 and base 25. Side rails 40 typically extend along the sides of platform 35, with side rails 40 being spaced from platform 35 on mounts 45. A cushion 50 is typically disposed on the top surface 52 of platform 35.

As noted above, surgical table 15 is generally formed out of a radiopaque material, e.g., metal. As a result, it is not possible to image patient anatomy using X-ray technology where the X-rays must pass through the surgical table. For practical purposes, this renders CT imaging impossible and significantly limits X-ray imaging to highly restricted angles of view.

In accordance with the present invention, and looking now at FIGS. 1-9, 9A and 9B, there is provided a novel table extender 10 for mounting to one end of surgical table 15. As will hereinafter be discussed, table extender 10 is constructed so that patient anatomy supported on table extender 10 can be imaged with X-ray technology through the table extender, thereby enabling CT imaging and X-ray imaging with substantially unlimited angles of view.

As seen in FIG. 1, table extender 10 is sized to support the patient from a point proximal to the hips of the patient to a point proximal to the knees of the patient, whereby to provide optimal support for hip distraction, particularly when the patient is positioned in the so-called "Trendelenburg position" during hip surgery.

Table extender 10 also provides increased flexibility in the ability to X-ray the hip joint from multiple viewpoints while the hip joint is supported on table extender 10.

In one preferred form of the invention, table extender 10 comprises a distal end 53 and a proximal end 54. More particularly, table extender 10 comprises a base 55 having a distal end 56 and a proximal end 57, a pair of mounts 60 for mounting base 55 to side rails 40 of surgical table 15, and a cushion 65 for disposition on base 55.

Base 55 preferably comprises a substantially rigid radiolucent material (e.g., a carbon fiber composite) such that X-ray and/or CT imaging may be performed on the anatomy residing on table extender 10, and base 55 is sufficiently strong to support a substantial portion of the patient's weight. See, for example, FIG. 9, which shows a C-arm X-ray machine 70 disposed about table extender 10 so that C-arm X-ray machine 70 can image anatomy supported on table extender 10. Base 55 of table extender 10 may comprise one or more openings, e.g., side openings 75 for enabling easy grasping of table extender 10 during mounting to, and dismounting from, surgical table 15, and/or for receiving straps of stabilizing pad 20 (see below), distal openings 80 for enabling other equipment to be mounted to table extender 10 (e.g., a post), etc.

Mounts 60 may be substantially any mounts which allow base 55 to be attached to, or detached from, surgical table 15 without significantly diminishing the overall radiolucency of table extender 10. In one form of the invention, each of the mounts 60 generally comprises a body 85 mounted to proximal end 57 of base 55 and extending proximally therefrom. Bodies 85 comprise slots 90 for receiving side rails 40 of surgical table 15. Clamps 95 are pivotally mounted to bodies 85, such that clamps 95 can be pivoted towards and away from bodies 85. Clamps 95 preferably comprise recesses 100 for disposition about mounts 45 of side rails 40 when side rails 40 are received in slots 90. In one form of the invention, mounts 60 comprise friction elements (not shown) which prevent clamps 95 from falling into their locked position until after the user deliberately pushes clamps 95 into their locked position. In one form of the invention, these friction elements comprise spring plungers which are adjusted so as to provide a degree of resistance to clamps 95 closing into their locked position. Alternatively, other sources of friction or resistance can be utilized such as interference fits between the machined components, ramps, springs, or additional materials such as rubber or silicone added to increase the friction locally. Locking screws 105 extend through bodies 85 and project into slots 90, whereby to enable mounts 60 to be secured to side rails 40 of surgical table 15.

Cushion 65 resides on base 55 of table extender 10. Cushion 65 preferably has a thickness (or height) which is substantially the same as the thickness (or height) of cushion 50 of surgical table 15. Cushion 65 is also formed out of a radiolucent material such that X-ray and/or CT imaging may be performed on the anatomy residing on table extender 10. If desired, a recess 107 may be provided in the distal portion of cushion 65 so as to expose distal openings 80 in base 55.

Due to the extensive use of radiolucent materials, table extender 10 is nearly completely radiolucent, i.e., the only portions of table extender 10 which are not radiolucent are mounts 60 (which are preferably formed out of a radiopaque metal, e.g., stainless steel). Significantly, the only portion of table extender 10 which is not radiolucent in the region extending away from surgical table 15 is the distal portions of mounts 60 (i.e., the portions of bodies 85 of mounts 60 which extend alongside or beneath base 55 of table extender 10). In one preferred form of the invention, greater than approximately 90% of the surface area of table extender 10 is radiolucent (as viewed from a vertical or anterior/posterior perspective). In another preferred form of the invention, greater than approximately 80% of the surface area of table extender 10 is radiolucent. Of particular note, the middle and distal portions of table extender 10 are completely radiolucent. In other words, the distal sections of mounts 60 do not extend to the middle and distal portions of table extender 10, and there is no metal reinforcement across the width of table extender 10 to support the patient's weight as with existing table extenders. The carbon fiber construction of base 55 of table extender 10 is able to support the weight of the anatomy carried by base 55 without requiring additional structural reinforcements. This is a significant improvement over the prior art as it allows for better imaging and maneuverability of the X-ray equipment; one example of the prior art is U.S. Pat. No. 8,944,065.

In one method of use, table extender 10 is grasped via side openings 75, and then table extender 10 is moved towards surgical table 15 so that slots 90 of mounts 60 are aligned with side rails 40 of surgical table 15. Note that clamps 95 of mounts 60 are pivoted upward relative to bodies 85 of mounts 60 as mounts 60 of table extender 10 are slid over side rails 40 of surgical table 15, with side rails 40 being received in slots 90 of mounts 60. When table extender 10 has been properly positioned relative to surgical table 15, clamps 95 are pivoted downwardly so that recesses 100 of clamps 95 seat over mounts 45 of side rails 40. Then locking screws 105 are used to further secure mounts 60 to side rails 40 (and hence to further secure table extender 10 to surgical table 15).

Thereafter, when a patient is positioned on surgical table 15 and table extender 10, the patient is supported by cushion 50 of surgical table 15 and cushion 65 of table extender 10, both of which are at least partially covered by stabilizing pad 20. Significantly, patient anatomy supported on table extender 10 may be imaged using X-ray and/or CT imaging due to the radiolucency of table extender 10. In addition, table extender 10 is preferably sized so as to support the patient from a point proximal to the hips to a point proximal to the knees (see FIG. 1), whereby to provide optimal support for hip distraction, particularly when the patient is positioned in the so-called "Trendelenburg position" during hip surgery.

The Trendelenburg position requires that surgical table 15 be tilted. In one preferred form of the invention, and looking now at FIGS. 9A and 9B, table extender 10 comprises an inclinometer 107A to show its angle of incline (and hence to show the angle of incline of surgical table 15).

In one preferred form of the invention, base 55 of table extender 10 is approximately 18-24 inches long, and more preferably approximately 21 inches long, and approximately 18-24 inches wide, and more preferably approximately 21.25 inches wide. Mounts 60 extend approximately 7 inches along the length of base 55 of table extender 10 (i.e., mounts 60 extend approximately 7 inches distal from the proximal edge of base 55 of table extender 10). In one preferred form of the invention, the patient is positioned such that their hip joint is approximately 7-15 inches distal to the proximal edge of base 55 of table extender 10. With a minimum of 7 inches spacing between the patient's hip joint and the proximal edge of base 55 of table extender 10, the patient's hip can be X-ray'd without interference from mounts 60, which is important inasmuch as mounts 60 are typically made of a radiopaque material such as stainless steel. The hip joint is preferably positioned proximal to the distal edge of base 55 of table extender 10; this provides some margin of safety from the possibility of the patient falling off the distal end of table extender 10 in the event the patient's hip moves distally on table extender 10. More particularly, when a distal distraction force is applied to the operative leg of the patient, the hip joint may shift slightly in the direction of the force (i.e., the hip joint may move slightly in the distal direction). Having a portion of table extender 10 distal to the hip joint provides a safety margin from the possibility of the hip joint sliding off the distal end of the table extender, resulting in the patient falling to the floor. In one preferred form of the invention, the patient's hip is positioned approximately one-third to approximately two-thirds of the distance distal to the proximal edge of base 55 of table extender 10.

It should be appreciated that there is a practical limit to the maximum length of table extender 10. If the table extender is too long, then more of the patient's body may be placed on the table extender, requiring the table extender to bear additional weight of the patient. This may require larger mounts 60 and/or increased thickness of base 55 of table extender 10, neither of which is desirable as they may decrease the radiolucency of the system. Also, an increased length to table extender 10 may require a distraction system which extends further away from surgical table 15. This is not preferred inasmuch as it generally increases the size and weight of the distraction system, making it more difficult to physically manipulate and manage by the hospital staff; and this is also not preferred inasmuch as the larger distraction system may not fit into some operating rooms (some older facilities have smaller operating rooms). In one form of the invention, base 55 of table extender 10 is approximately as long as the average length of a human femur bone (which is approximately 19 inches long).

Stabilizing Pad 20

Looking next at FIGS. 1-3, 10 and 11, stabilizing pad 20 is provided to cover the top surface of surgical table 15, and the top surface of table extender 10, so as to increase the friction between the patient and surgical table 15/table extender 10, whereby to reduce the possibility of the patient inadvertently sliding on surgical table 15 and table extender 10, particularly during hip distraction and/or leg manipulation and/or during "Trandelenburg positioning". Note that stabilizing pad 20 is placed on top of cushion 50 of surgical table 15 and cushion 65 of table extender 10. Note also that while stabilizing pad 20 is shown in the figures as extending past the patient's head, stabilizing pad 20 can terminate at another location, e.g., in the mid-back region of the patient.

In one preferred form of the invention, stabilizing pad 20 comprises a bottom surface 108 for contacting surgical table 15 (i.e., cushion 50 of surgical table 15) and table extender 10 (i.e., cushion 65 of table extender 10), and a top surface 109 for receiving the patient. Bottom surface 108 preferably comprises a high friction material for preventing stabilizing pad 20 from sliding relative to surgical table 15 (i.e., relative to cushion 50 of surgical table 15) and table extender 10 (i.e., relative to cushion 65 of table extender 10). Top surface 109 preferably comprises a high friction material for preventing a patient from sliding relative to stabilizing pad 20. It should be appreciated that top surface 109 of stabilizing pad 20 is made of a material which is suitable for contacting the skin of a patient, with respect to both patient compatibility and comfort, while also increasing friction with the patient. In one preferred form of the invention, top surface 109 of stabilizing pad 20 is made of an open cell polyurethane foam.

In one preferred form of the invention, stabilizing pad 20 comprises a foam base 110 (which includes the aforementioned bottom surface 108) and a foam upper 115 (which includes the aforementioned top surface 109). In one preferred form of the invention, foam base 110 is sufficiently dense to provide a stable contact with cushion 50 of surgical table 15 and with cushion 65 of table extender 10, and foam upper 115 is flexible enough to allow the patient to sink into the stabilizing pad, increasing the overall contact and effective frictional resistance to sliding in a relatively stable support structure. It should be noted that some foam materials and shapes may be superior for creating sliding friction against human skin, while other materials and shapes may be superior for creating sliding friction against the top surfaces of surgical table 15 and table extender 10. In one preferred form of the invention, foam upper 115 is an open cell polyurethane foam comprising an "egg crate" top surface 109 so as to further enhance friction between the patient and stabilizing pad 20 while still being comfortable for contacting the skin of the patient. And in one preferred form of the invention, foam base 110 is preferably a closed cell foam (e.g., ethylene-vinyl acetate (EVA)) comprising a flat bottom surface 108. In one preferred form of the invention, foam base 110 has a higher density than foam upper 115. It should be appreciated that, by forming foam base 110 out of a higher density closed cell foam (e.g., ethylene-vinyl acetate (EVA)) and by forming foam upper 115 out of a lower density open cell foam (e.g., polyurethane foam) allows the foam base to provide a stable, high friction foundation on surgical table 15 and allows foam upper 115 to provide a contouring, high friction support beneath and around the patient.

In one preferred form of the invention, hook-and-loop fasteners 120 are used to secure stabilizing pad 20 to cushion 50 of surgical table 15 and to cushion 65 of table extender 10.

And in one preferred form of the invention, straps 125 are used to secure stabilizing pad 20 to surgical table 15 and to table extender 10, for example, securing stabilizing pad 20 to side rails 40 of surgical table 15 and/or side openings 75 of table extender 10.

Patient Strap 22

Figure 10:
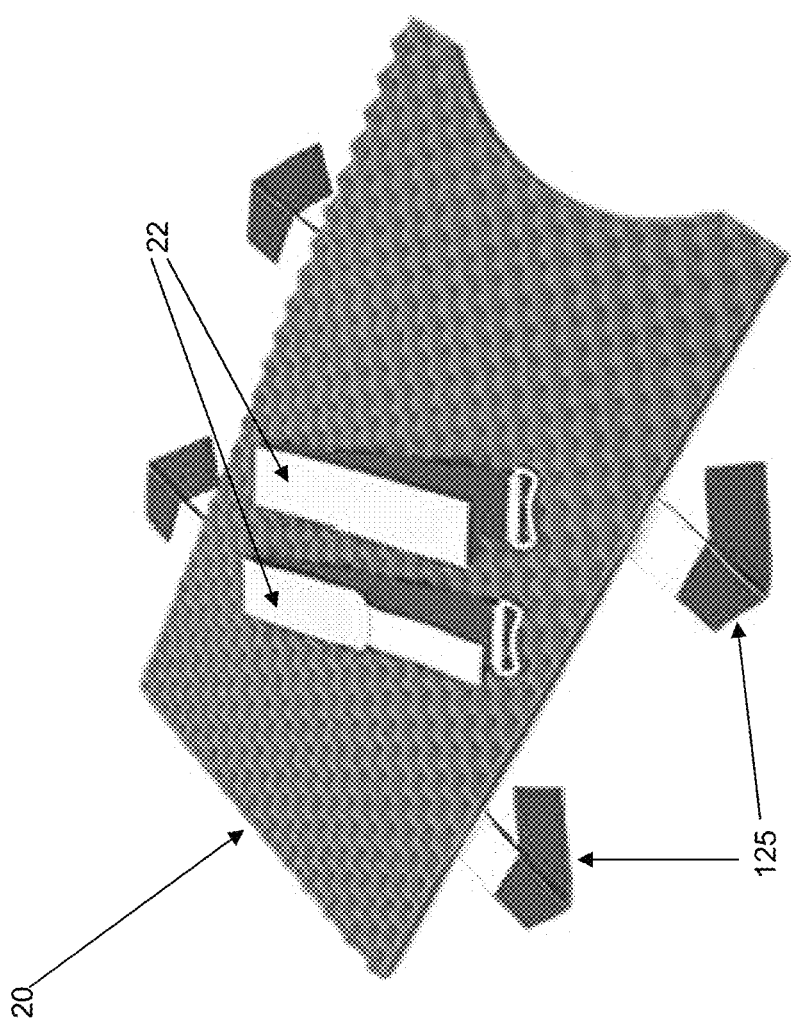
FIGS. 10 and 11 are schematic views showing further details of the stabilizing pad of the novel system shown in FIGS. 1-4.

Still looking at FIGS. 1 and 10, in one form of the invention, one or more patient straps 22 are also provided to secure the patient to surgical table 15. More particularly, one or more patient straps 22 may be passed over the torso of the patient, under the arms of the patient and attached to surgical table 15. Patient straps 22 prevent the patient from rolling on surgical table 15. Patient straps 22 may also be made so as to prevent the patient from sliding longitudinally on the surgical table. Thus, patient straps 22 provide a counterforce to the anatomy during post-less hip distraction. In addition, patient straps 22 provide an added margin of safety for the patient during a Trendelenburg procedure when surgical table 15 is tilted so that the patient's head is angled towards the floor and the patient's feet are angled towards the ceiling, i.e., to prevent the patient from sliding or rolling on surgical table 15.

If desired, patient straps 22 may extend completely around platform 35 of surgical table 15. Additionally and/or alternatively, patient straps 22 may be configured for attachment to side rails 40 of surgical table 15, e.g., the ends of patient straps 22 may be provided with hook-and-loop fasteners for securing patient straps 22 to side rails 40 of surgical table 15.

Stabilizing Pad with Handles

Figure 11:
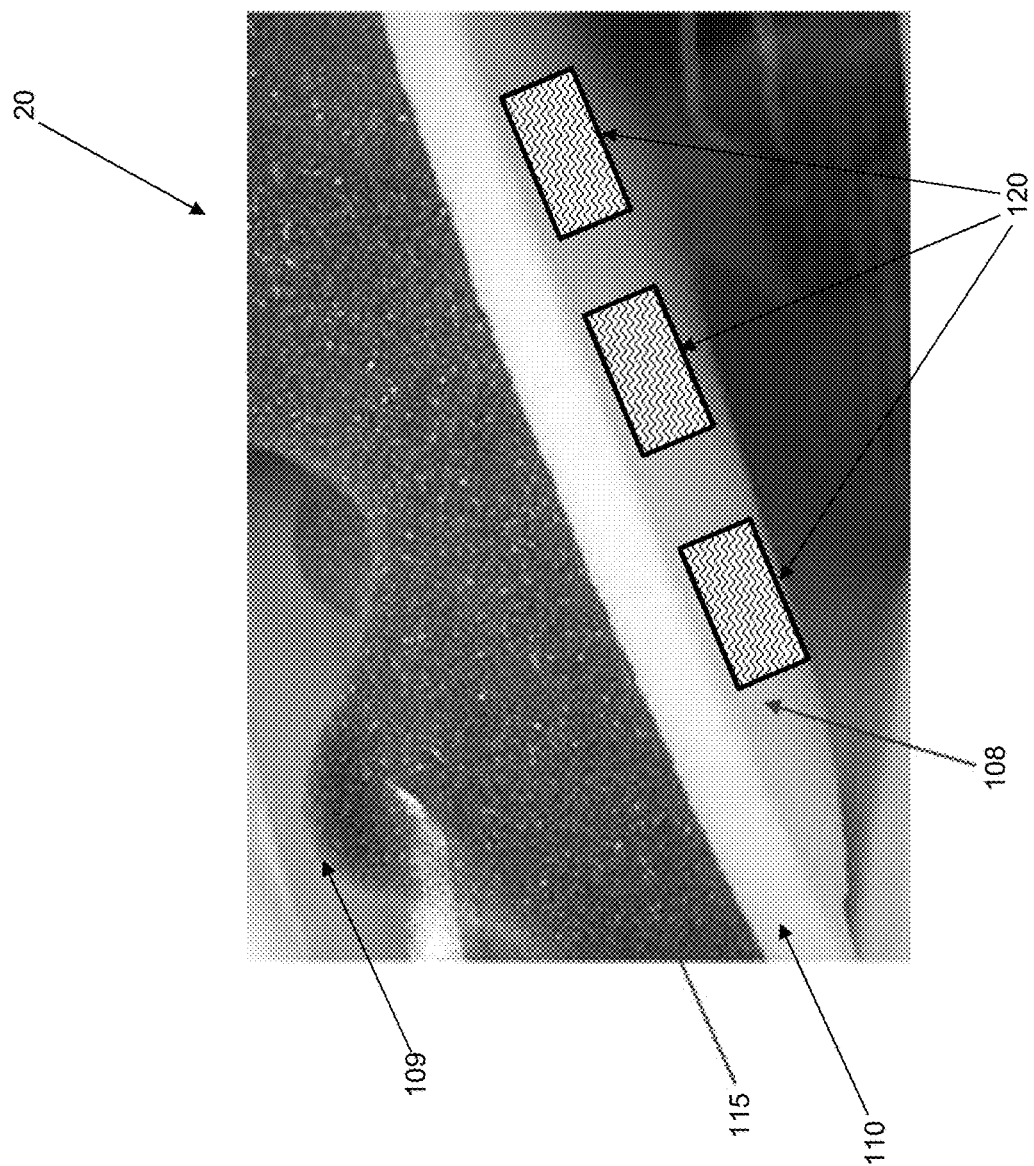
Figure 11A:
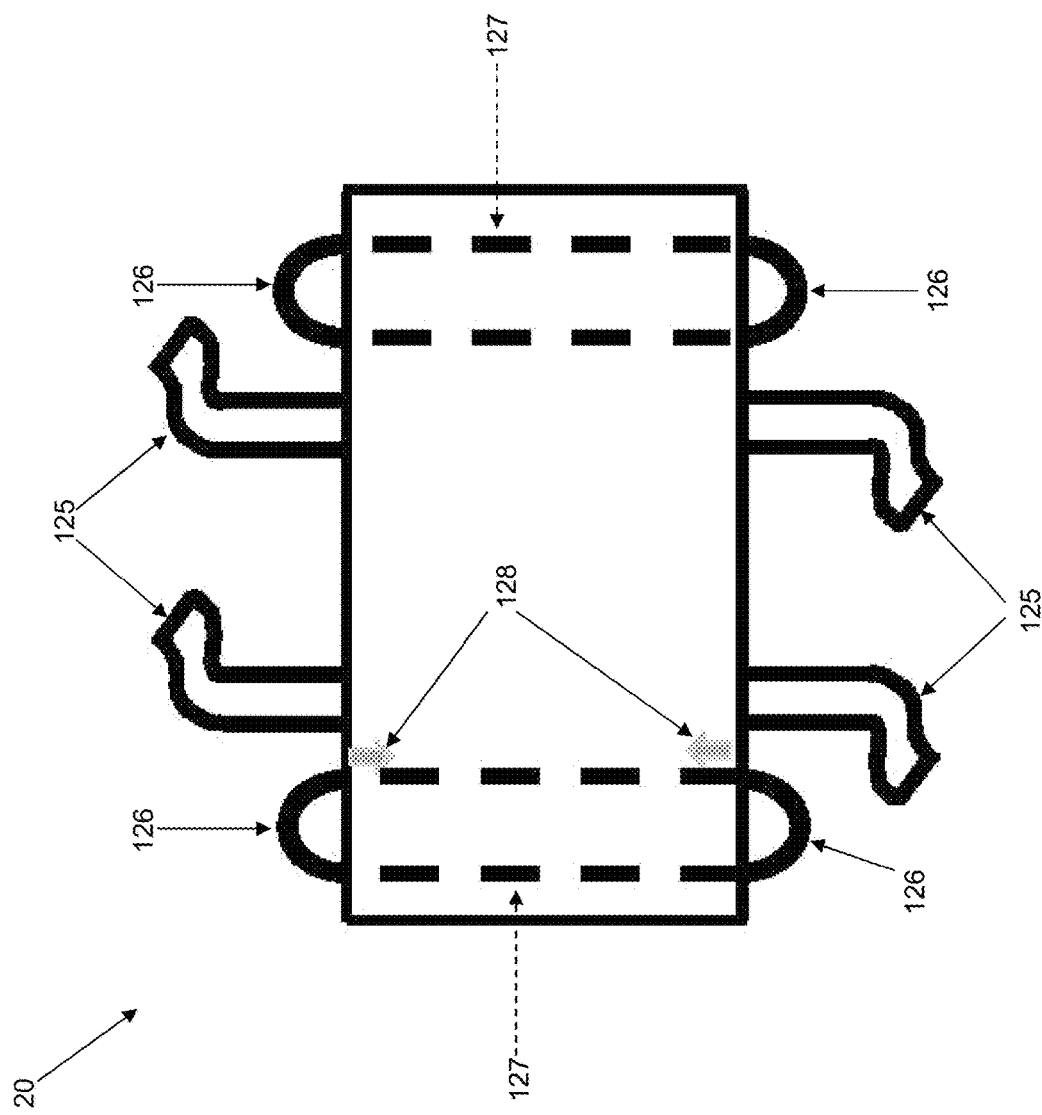
FIGS. 11A and 11B are schematic views showing another stabilizing pad formed in accordance with the present invention.
Figure 11B:
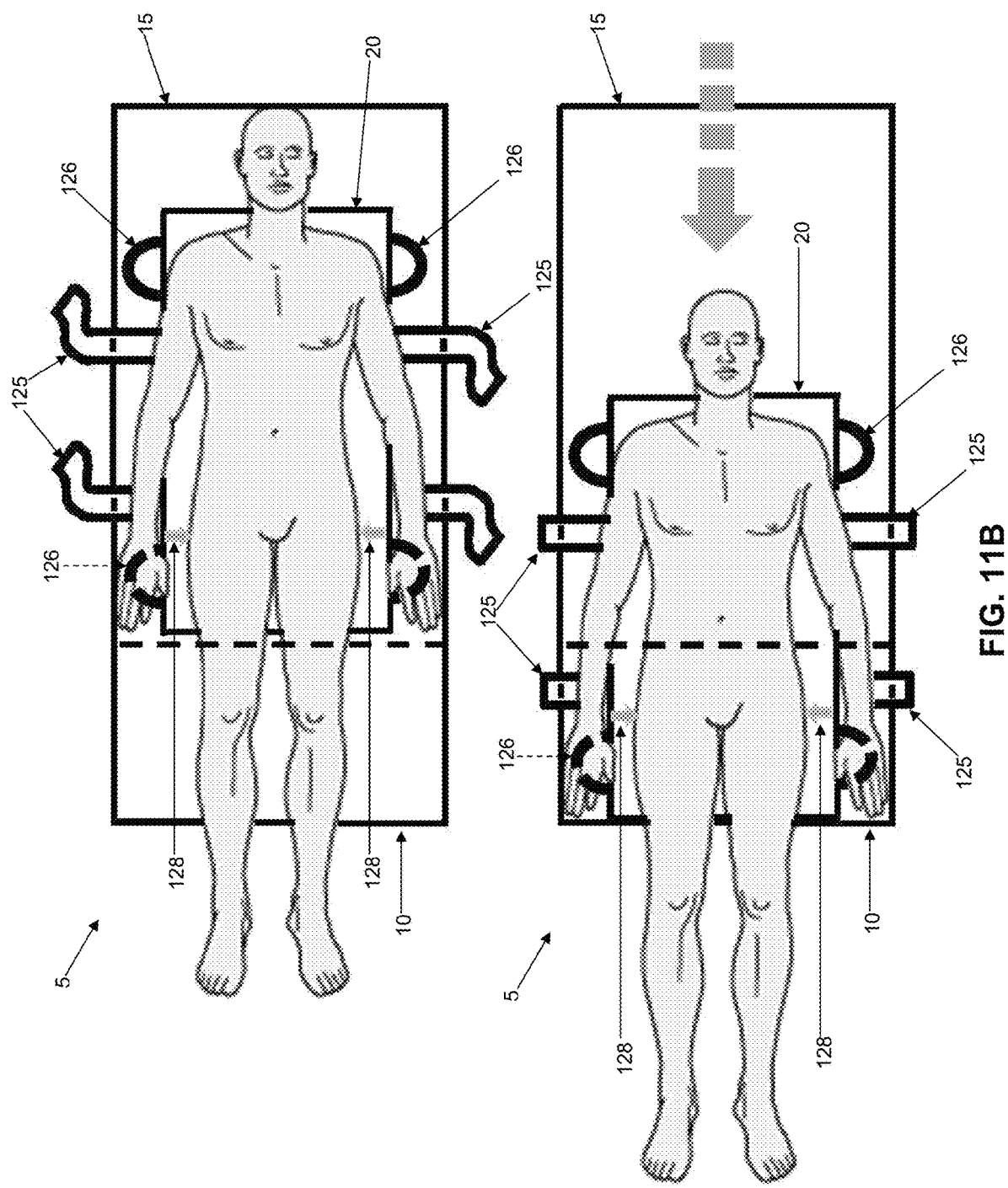

In another form of the invention, and looking now at FIGS. 11A and 11B, stabilizing pad 20 further comprises handles (or grips) 126. In transferring a patient onto, and off of, surgical table 15 (e.g., from a gurney), it is common practice to transfer the patient such that their entire body is initially supported by surgical table 15 and table extender 10 while the surgical staff continues preparations for surgery. Once the patient is ready to be connected to the distraction apparatus (i.e., mounting their feet into the surgical boots of the distraction apparatus and connecting the surgical boots to pulling elements of the distraction apparatus), the surgical staff slides the patient distally on surgical table 15 until the patient's hips are properly positioned on table extender 10 (e.g., in the manner described above). Typically the patient's knees will be just off table extender 10 (e.g., in the manner also described above). Normally this transfer of the patient from a more cephalad position on the surgical table during preparation to a more distal (caudal) position on the surgical table for distraction does not present a problem: most surgical tables have a cushion (e.g., cushion 50) on top of platform 35 of the surgical table, and this cushion can typically accommodate sliding a patient on cushion 50. However, stabilizing pad 20 has a higher degree of friction than a standard cushion; therefore, it may be too difficult to slide the patient on stabilizing pad 20 and the surgical staff must resort to lifting the patient in order to move the patient relative to surgical table 15 and table extender 10. This is not desirable as it can lead to back injuries for the surgical staff.

To this end, in one form of the invention, and looking now at FIG. 11A, stabilizing pad 20 comprises handles 126 which can be utilized to slide the stabilizing pad (and hence the patient) along cushion 50. See FIG. 11B. Stabilizing pad 20 may comprise reinforcement structures 127 between opposing handles 126 so that stabilizing pad 20 can support the patient's weight (e.g., a strap 127 extending across the width of the pad from one handle 126 to another handle 126 located on the opposite side of stabilizing pad 20). Alternatively, stabilizing pad 20 may comprise a sheet of strong material (not shown) interposed between foam base 110 and foam upper 115, e.g., a strong sheet of material interposed between a foam base 110 and a foam upper 115.

In one preferred form of the invention, stabilizing pad 20 may comprise one or more markings 128 for indicating the preferred location of the patient's hip joints on stabilizing pad 20 in the caudal/cephalad direction. These markings 128 help ensure that, once stabilizing pad 20 (with the patient thereon) is moved to the surgical position, the patient's hip joints will be located on table extender 10 in the preferred position (i.e., proximal to mounts 60 yet spaced from the distal edge of base 55 of table extender 10).

Low-Friction (e.g., Lubricious) Transfer Sheet

Figure 11C:
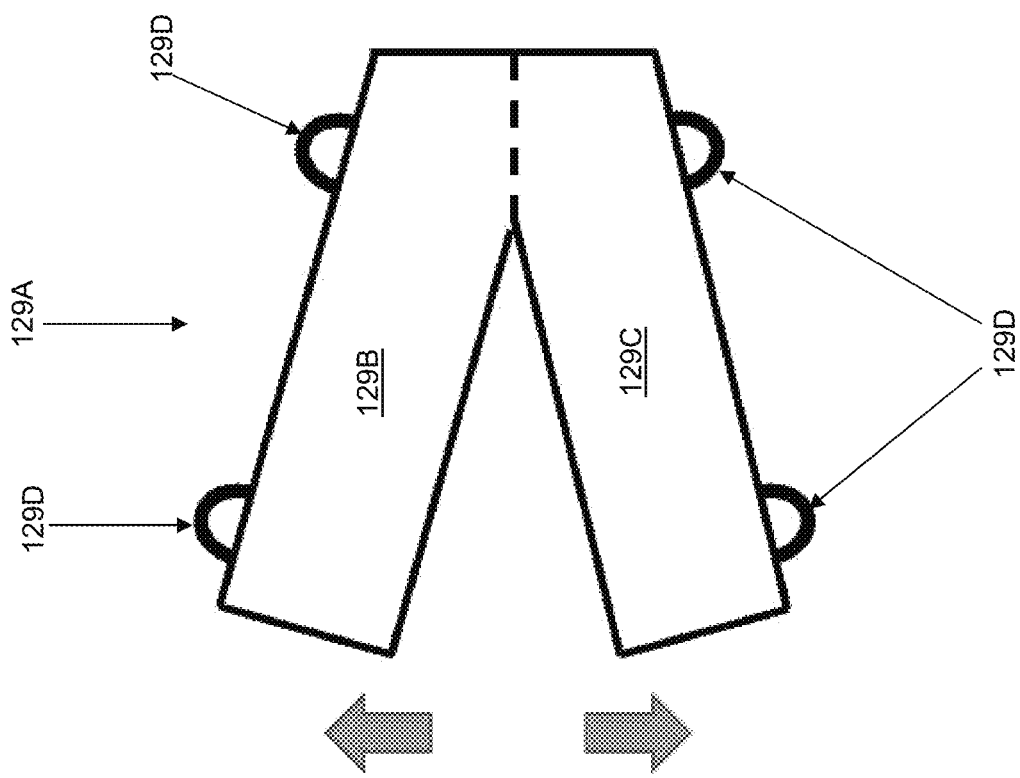
FIG. 11C is a schematic view showing a transfer sheet which may be used in conjunction with the stabilizing pads of the present invention.
Figure 11C:
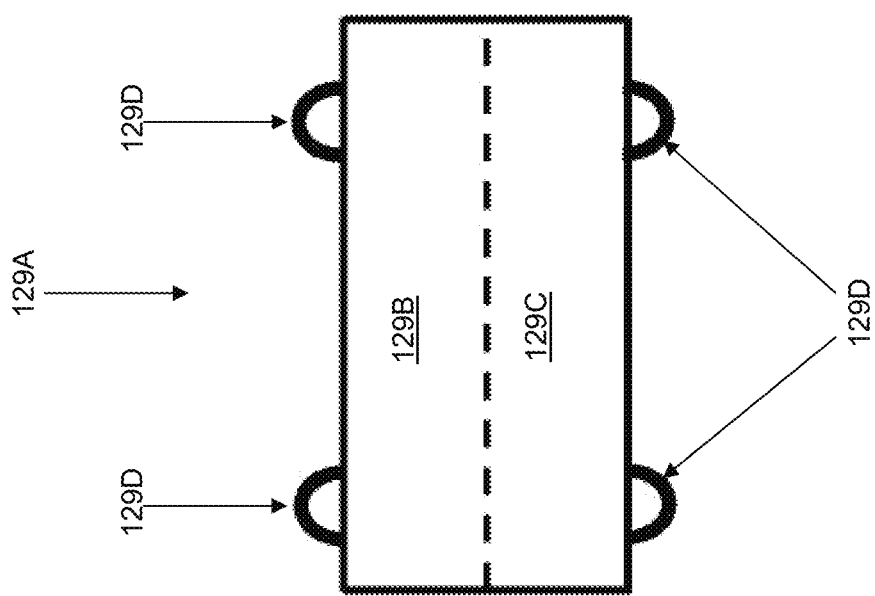

In another form of the invention, a low-friction (e.g., lubricious) transfer sheet 129 (FIGS. 11C and 11D) is disposed between the patient and stabilizing pad 20 before and during patient transfer, and then the low-friction (e.g., lubricious) transfer sheet is removed prior to the start of the surgery (including distraction of the hip).

More particularly, stabilizing pad 20 is placed on, and secured to, surgical table 15 in the surgical position. In order to slide the patient from the more cephalad initial position (used during patient preparation) to the more caudal surgical position (used for distraction and surgery), a low-friction (e.g., lubricious) transfer sheet 129 (FIGS. 11C and 11D) can be used. However, this low-frication (e.g., lubricious) transfer sheet 129 must be removed from beneath the patient after patient transfer and prior to distraction in order to prevent the patient from sliding on the low-friction (e.g., lubricious) transfer sheet during table tilting and/or distraction, but the low-friction (e.g., lubricious) transfer sheet may be difficult to remove from under the patient due to the patient's weight. Therefore, in one embodiment, and looking now at FIG. 11C, low-friction (e.g., lubricious) transfer sheet 129 may comprise a split-away construction 129A so that the low-frication (e.g., lubricious) transfer sheet can split into 2 or more sections 129B, 129C which can more easily be removed from under the patient. In this embodiment, low-friction (e.g., lubricious) transfer sheet 129 is placed on surgical table 15. The patient is transferred from their gurney onto low-frication transfer sheet 129 (which rests on surgical table 15) in a typical prep position with their body caudal to the surgical position. After prep is completed and the patient is to be moved to the surgical position, the surgical staff then slides the patient down to the surgical position using low-friction (e.g., lubricious) transfer sheet 129. Low-friction transfer sheet 129 is then removed from under the patient using the split-away construction 129A.

Note that low-friction (e.g., lubricious) transfer sheet 129 is preferably provided with handles 129D to facilitate movement of the low-friction transfer sheet (and hence movement of a patient disposed on the low-friction transfer sheet 129).

Figure 11D:
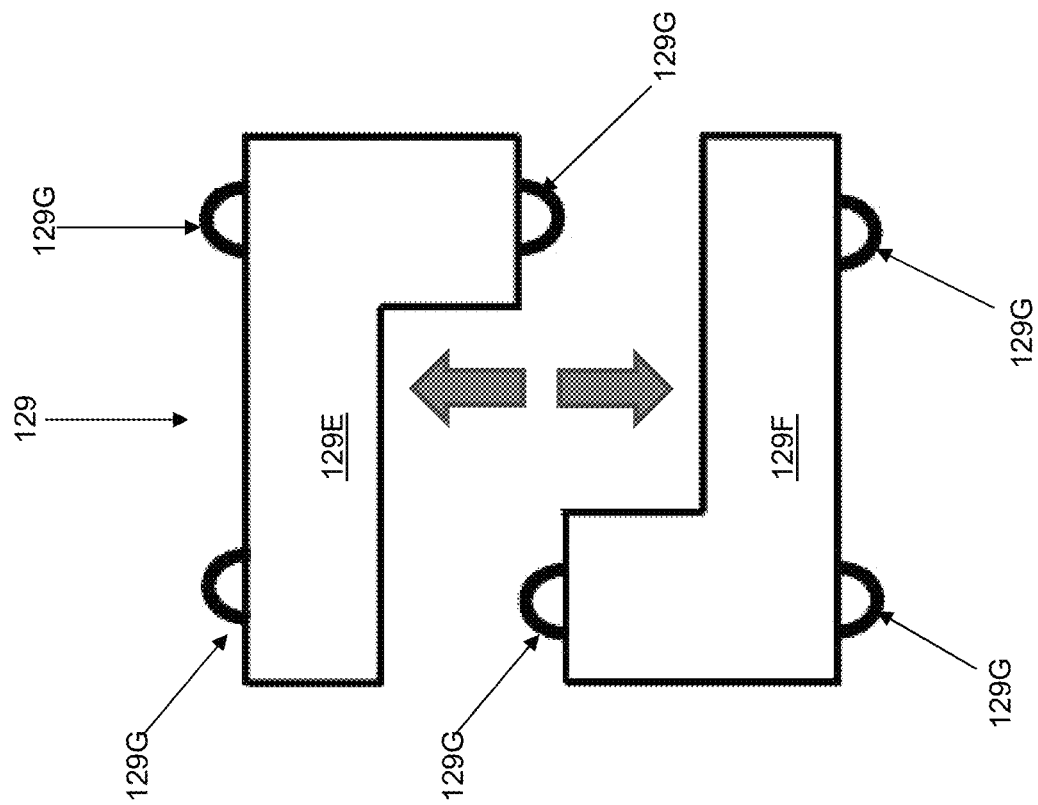
FIG. 11D is a schematic view showing another transfer sheet which may be used in conjunction with the stabilizing pads of the present invention.
Figure 11D:
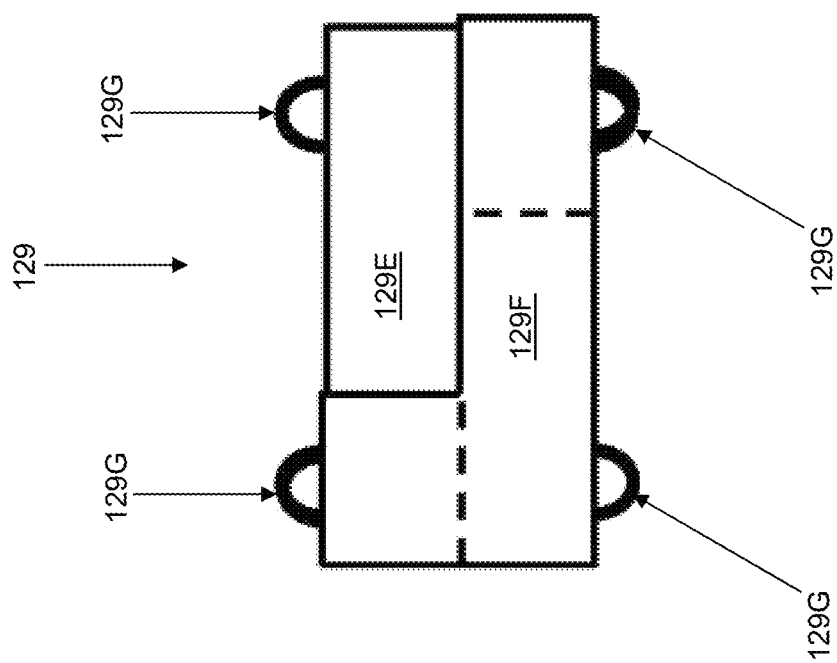

In another form of the invention, and looking now at FIG. 11D, low-friction (e.g., lubricious) transfer sheet 129 may comprise sections 129E and 129F which are initially coupled together via their overlapping handles 129G and which can be pivoted or pulled out from under the patient when the low-friction transfer sheet 129 is to be removed.

Stabilizing Pad with Raised Sections

Figure 12:
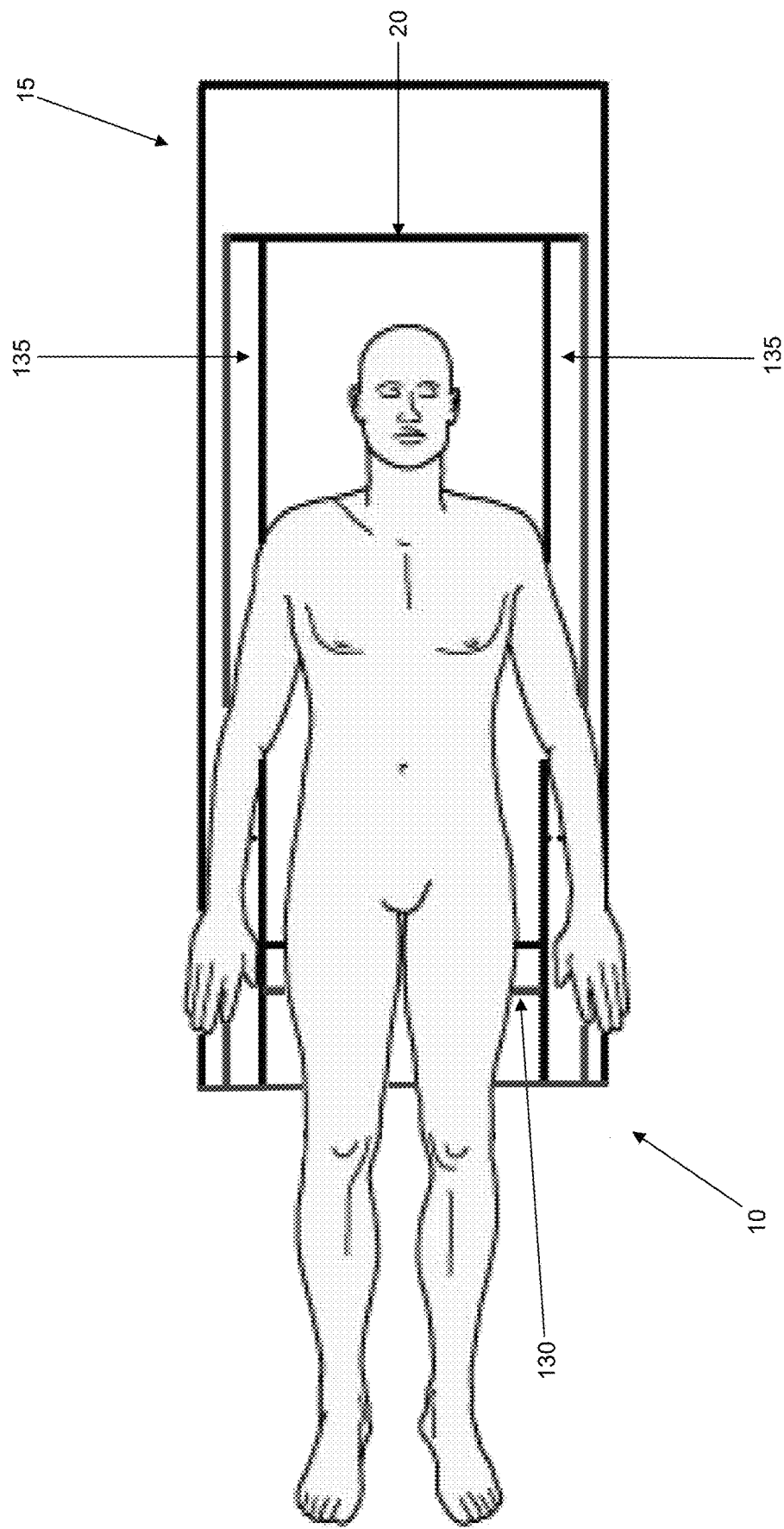
FIGS. 12-14 are schematic views showing another stabilizing pad formed in accordance with the present invention.
Figure 13:
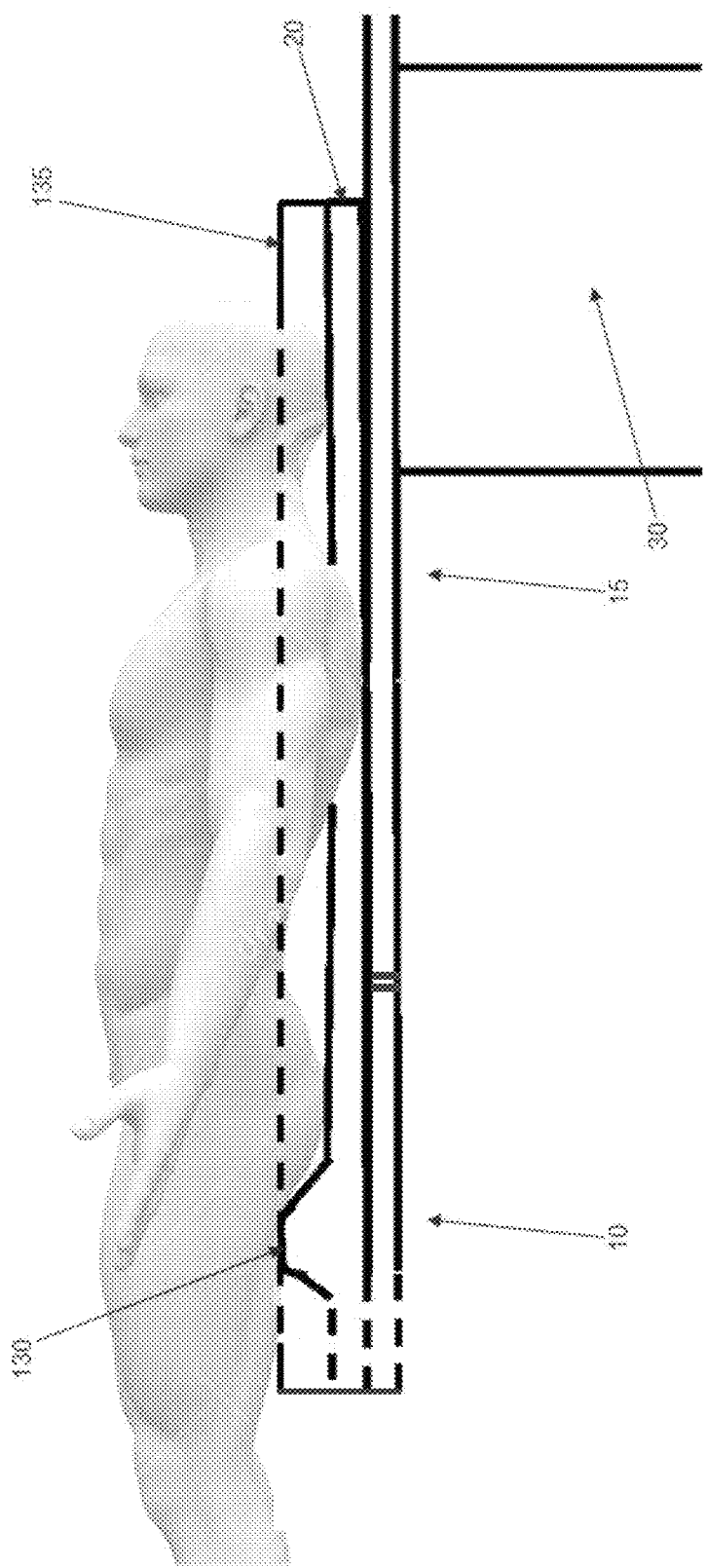
Figure 14:
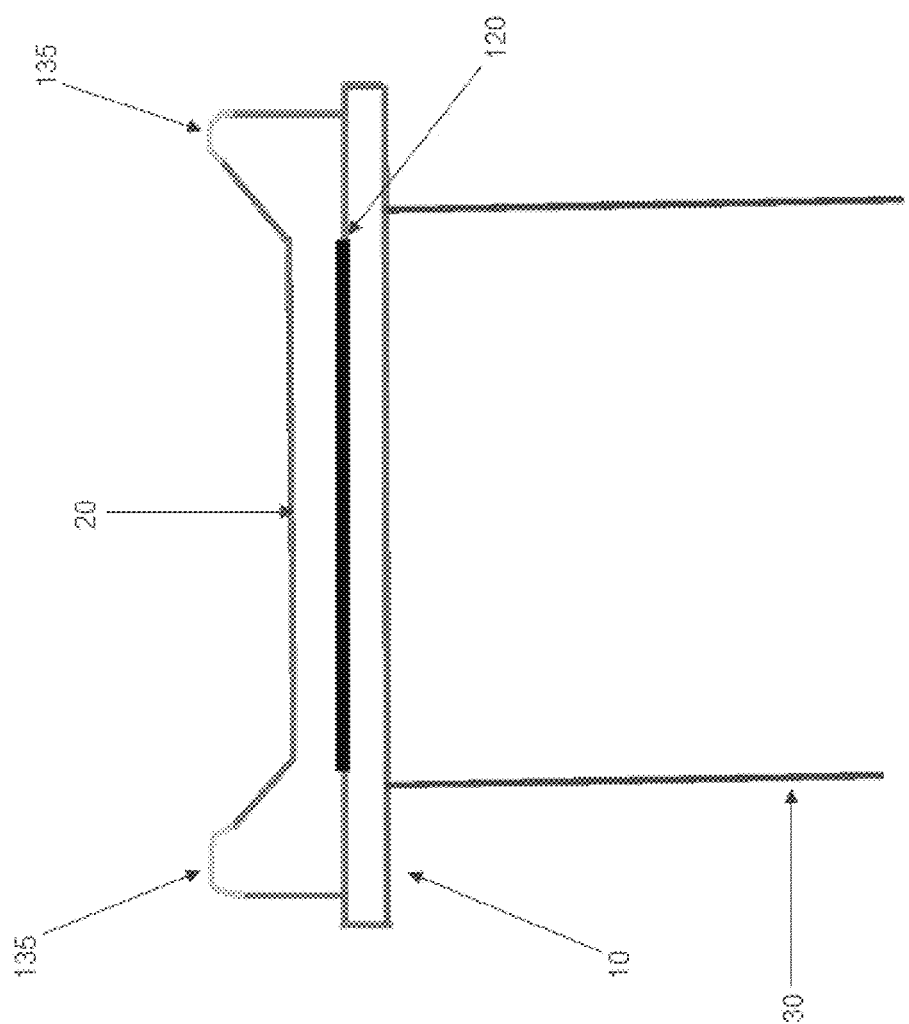

In another form of the invention, and looking now at FIGS. 12-14, stabilizing pad 20 may comprise (i) a raised distal section 130 near its distal end, and/or (ii) raised lateral sections 135 on each side of the patient.

Raised distal section 130 of stabilizing pad 20 functions as a stop to resist movement of the patient distally, e.g., raised distal section 130 provides a counterforce to the anatomy during hip distraction.

Raised lateral sections 135 of stabilizing pad 20 function as lateral stops which resist movement of the patient sliding or rolling laterally, e.g., raised lateral sections 135 add an extra margin of safety for post-less hip distraction where there is no padded post to keep the patient from sliding laterally on surgical table 15.

It should be appreciated that, inasmuch as raised lateral sections 135 may limit access to surgical portals and/or restrict hand movements by the surgical team, raised lateral sections 135 may extend along only portions of the patient's sides, e.g., in the case of hip surgery, raised lateral section 135 may extend along the torso of the patient but terminate at, or proximal to, the hip region of the patient.

Raised lateral sections 135 are preferably provided on both sides of stabilizing pad 20. However, if desired, stabilizing pad 20 may provide a raised lateral section 135 on only one side of the patient, e.g., on the operative leg side of the patient, or on the non-operative leg side of the patient.

When stabilizing pad 20 comprises a raised distal section 130 and/or raised lateral sections 135, stabilizing pad 20 may be constructed out of a gel material (e.g., a gel material such as that used to form cushions 50 and 65) so as to give raised sections 130 and/or 135 the requisite firmness. Note that inasmuch as raised sections 130 and/or 135 serve to keep the patient from sliding on the surgical table, the need for forming the stabilizing pad out of a high friction material is reduced. Thus, where raised sections 130 and/or 135 are provided, the stabilizing pad may be formed out of a material which is not a high friction material. Of course, it should also be appreciated that a stabilizing pad 20 comprising raised sections 130 and/or 135 may also be constructed out of high friction materials such as is described above, so as to further prevent the patient from sliding on the stabilizing pad.

Leg Support

A hip arthroscopy surgical patient is typically brought into the operating room on a gurney, then transferred to the surgical table with, for example, a transfer board or transfer sheet. In a hip arthroscopy procedure, the patient is typically transferred to a position on the table that supports most, if not all, of the full body length of the patient. Subsequently, the patient is moved distally when the feet are ready to be secured to the surgical boots of the distraction system.

In an alternative approach, the patient is transferred directly to their final position on the surgical table (i.e., the position the patient will be in for surgery). For hip arthroscopy this often involves a portion of the legs being suspended (i.e., the patient's torso and thighs may be on the surgical table, and the patient's feet may be suspended at the distal end of the surgical table). This can be accomplished by the patient walking into the operating room under their own power and placing themselves on the surgical table. In this approach, stabilizing pad 20 may be set in its surgical position at the time the patient is to place themselves on the surgical table, with stabilizing pad 20 comprising markings 128 indicating the desired position for the patient's hip joints. However, in this scenario, the legs of the patient extend past distal end 53 of table extender 10 and are unsupported for a time period prior to being secured to the surgical boots of the distraction system. This is undesirable as it may be uncomfortable for the patient and/or pose a risk of the patient falling off the surgical table.

Figure 15:
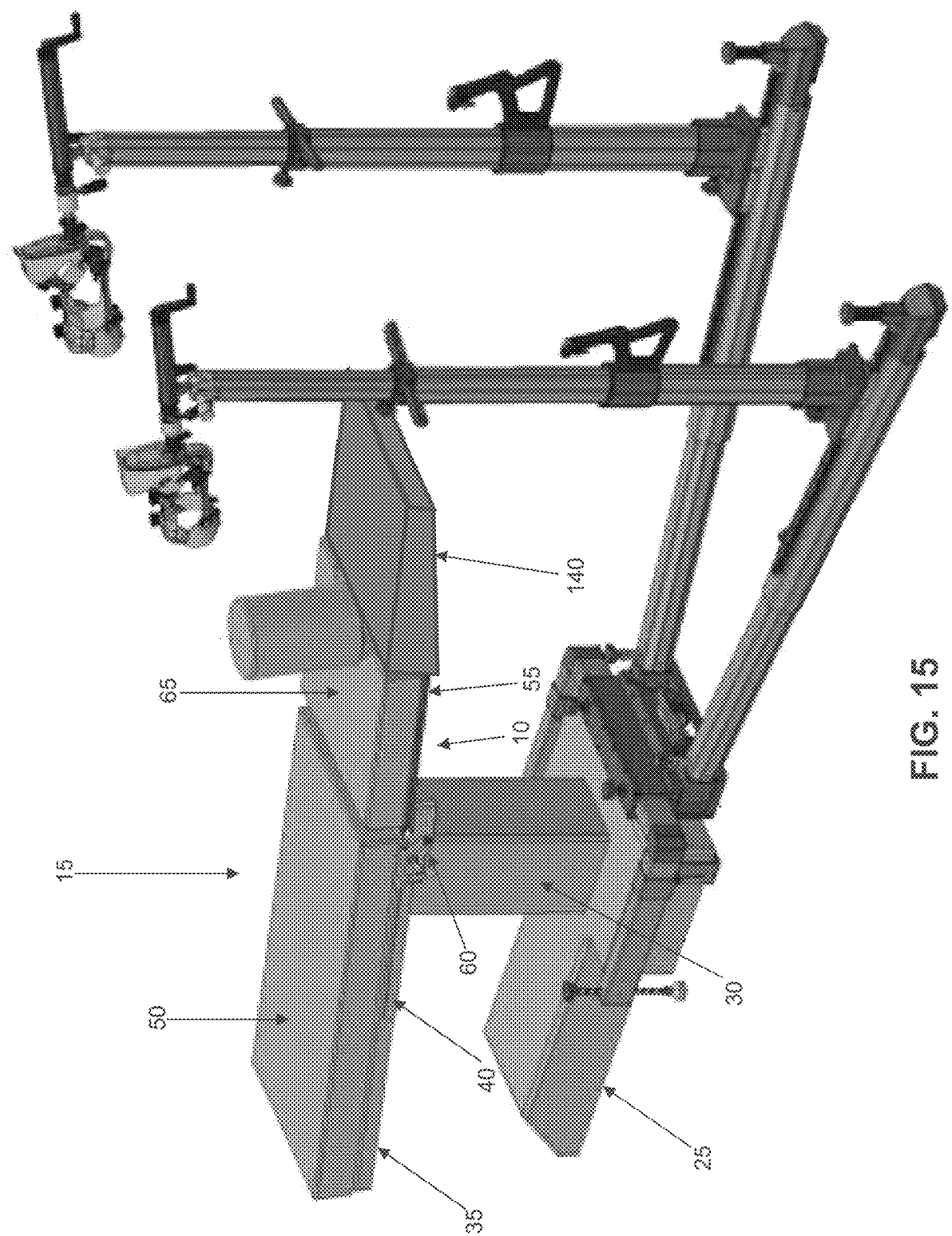
FIG. 15 is a schematic view showing a leg support formed in accordance with the present invention.

Therefore, in another form of the invention, and looking now at FIG. 15, a leg support 140 can be provided to support the patient's legs until such time as the patient's legs are secured in the distraction apparatus. In one form of the invention, leg support 140 is a tray which mounts to distal end 53 of table extender 10 and extends distally of table extender 10. Alternatively, leg support 140 may mount to surgical table 15 and extend distally of table extender 10. Leg support 140 may also have a support (not shown) which extends to the floor for additional support.

Figure 16:
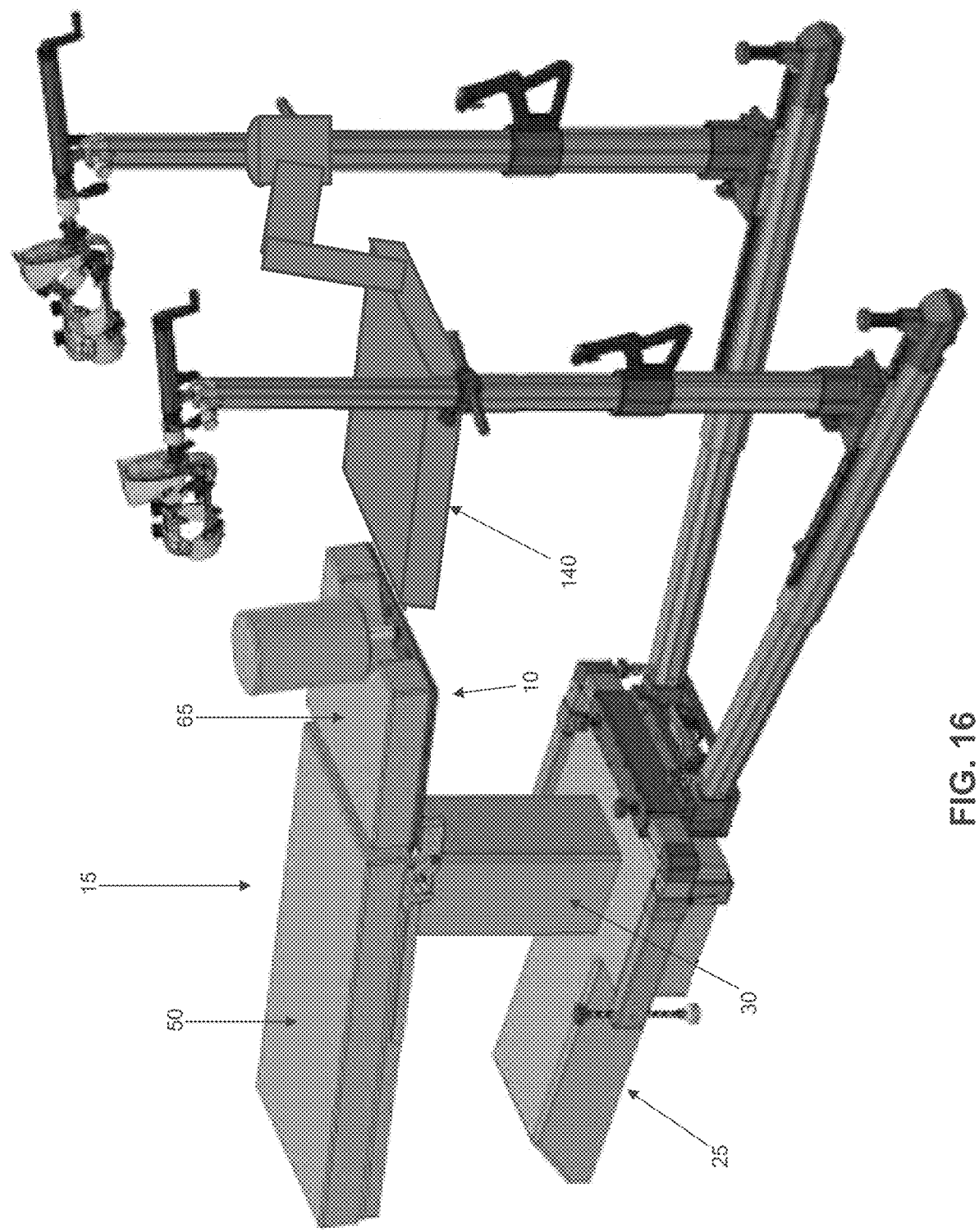
FIG. 16 is a schematic view showing another leg support formed in accordance with the present invention.

In another form of the invention, and looking now at FIG. 16, leg support 140 comprises a board or boards which mount to the distraction apparatus.

In these embodiments, leg support 140 may be readily connected to, and disconnected from, table extender 10, surgical table 15 or the distraction apparatus.

Figure 17:
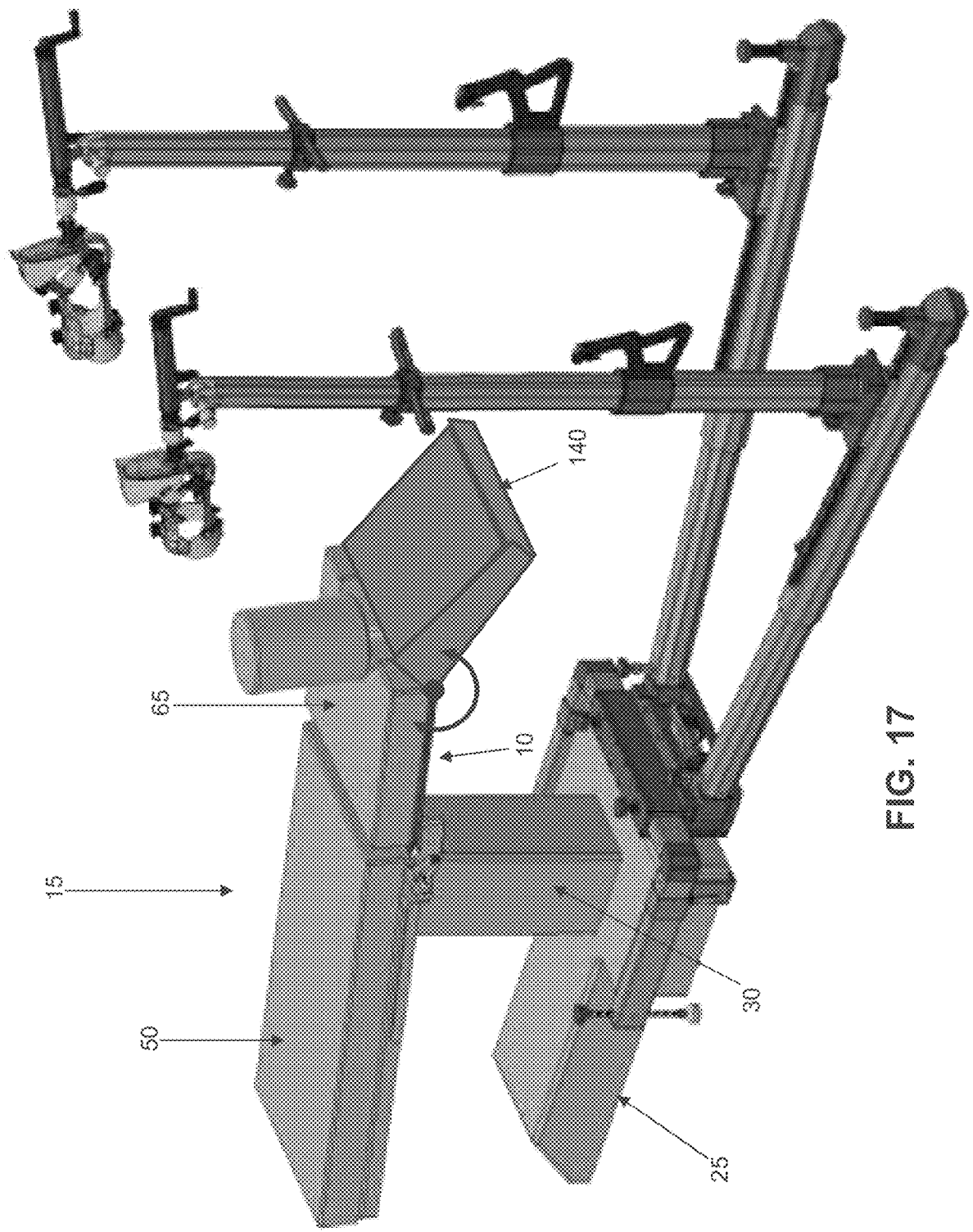
FIG. 17 is a schematic view showing a leg support formed as part of the table extender.
Figure 18:
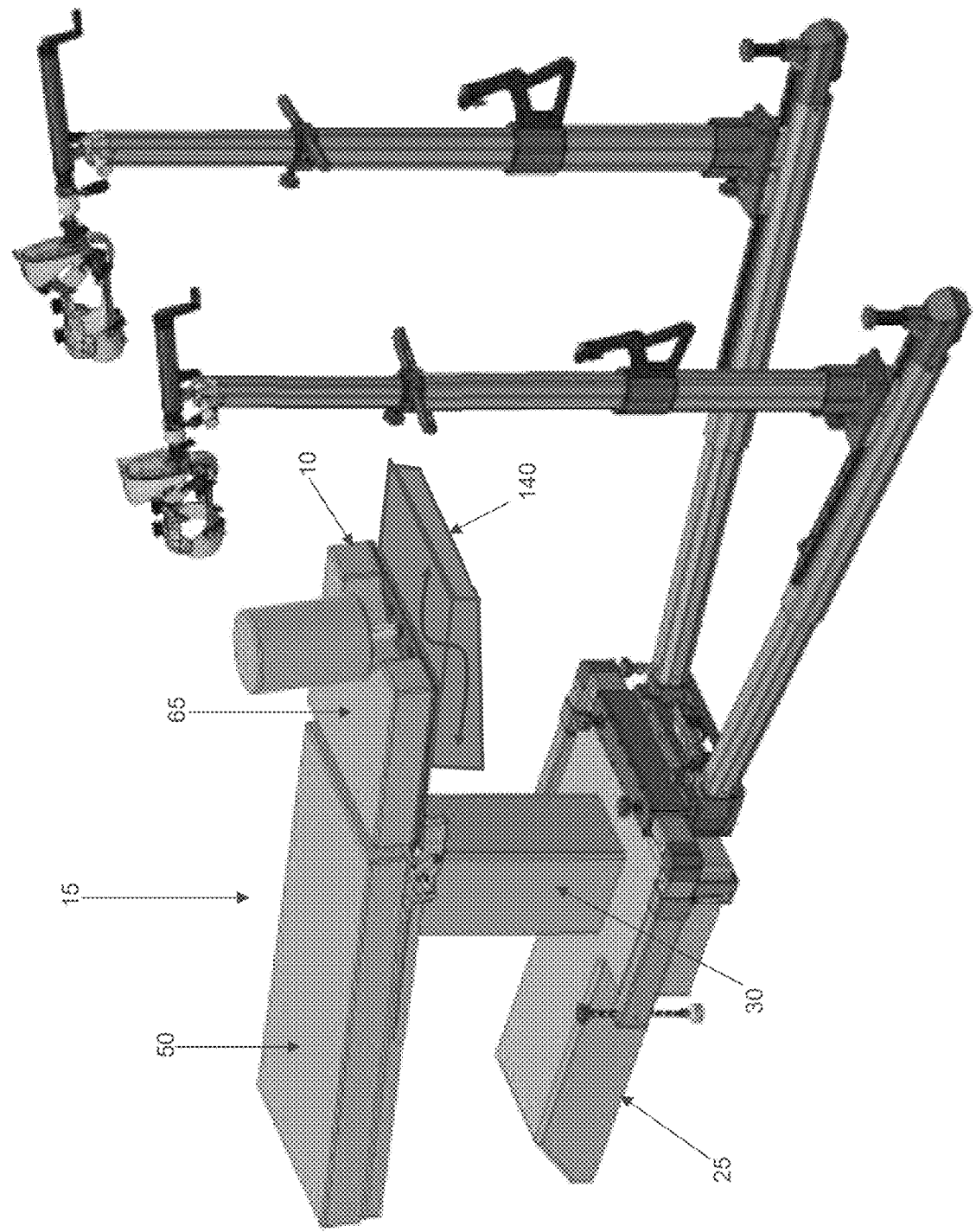
FIG. 18 is a schematic view showing another leg support formed as part of the table extender.

In yet another form of the invention, and looking now at FIGS. 17 and 18, leg support 140 is incorporated into table extender 10 itself; for example, leg support 140 may be in the form of a pivoting member which pivots relative to base 55 of the table extender (see FIG. 17), or leg support 140 may be in the form of a sliding member which slides and raises into a cantilevered position relative to base 55 of the table extender (see FIG. 18).

In one form of the invention, leg support 140 extends between 15 and 30 inches from the distal edge of table extender 10. In one preferred form of the invention, leg support 140 extends approximately 20 inches from the distal edge of table extender 10.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention. For example, a patient can also be positioned in a lateral decubitus position on the surgical table as opposed to a supine position.

What is claimed is:

1. A table extender, the table extender comprising:
a base configured for extending beneath hips of a patient, the base comprising:
a proximal portion for positioning adjacent to a surgical table,
a distal portion disposed opposite the proximal portion and comprising one or more openings for optional mounting of a perineal post, and
an intermediate portion disposed between the proximal portion and the distal portion,
wherein the base of the table extender is radiolucent;
a cushion mounted to the base; and
mounts configured for user releasable mounting of the base to side rails of a surgical table so that the base can support the hips of the patient, the side rails extending longitudinally along and being spaced from sides of a platform of the surgical table, wherein the mounts comprise slotted clamps configured to slide longitudinally along the side rails when mounting, and the mounts are configured to mount the table extender in only one orientation with respect to the surgical table in which a top surface of the cushion is aligned with a top surface of the surgical table that contacts the patient,
wherein the base and cushion have a rectangular shape so that the hips of the patient can be positioned entirely on the top surface of the cushion.

2. The table extender of claim 1, wherein the table extender comprises at least one marking for indicating the desired position of the hip joints of a patient on the table extender.

3. The table extender of claim 1, wherein the table extender is approximately the length of a human femur.

4. The table extender of claim 1, wherein the table extender is configured to enable a lateral X-ray of a patient's hip without image obstruction.

5. The table extender of claim 1, further comprising a leg support mounted to the distal portion of the table extender.

6. The table extender of claim 5, wherein the leg support is detachable from the table extender.

7. The table extender of claim 5, wherein the leg support is extendable and retractable relative to the table extender.

8. The table extender of claim 5, wherein the leg support is pivotally mounted to the distal portion of the table extender.

9. The table extender of claim 1, wherein the table extender comprises at least one inclinometer for indicating the angular disposition of the table extender and the surgical table relative to a floor.

10. The table extender of claim 9, wherein the at least one inclinometer is mounted on at least one of the mounts.

11. The table extender of claim 1, wherein the table extender is sized to support a patient from a point proximal to the hips of the patient to a point proximal to the knees of the patient.

12. The table extender of claim 10, wherein the at least one inclinometer is attached to the proximal portion of the table extender.

13. The table extender of claim 1, wherein the table extender is sized so that when a patient is disposed on the table extender, the hip joint of the patient will be positioned proximal to the distal portion of the table extender.

14. The table extender of claim 1, wherein the distal portion of the table extender and the intermediate portion of the table extender are substantially radiolucent.

15. The table extender of claim 1, wherein greater than approximately 80% of the surface area of the table extender is radiolucent.

16. The table extender of claim 1, wherein the table extender comprises at least one or more openings.

17. The table extender of claim 16, wherein the at least one more openings comprise side openings for enabling easy grasping of the table extender and/or for receiving straps of a stabilizing pad.

18. The table extender of claim 16, wherein the at least one more openings comprise a distal opening for enabling other equipment to be mounted to the table extender.

19. The table extender of claim 1, wherein the slotted clamps comprise hand screws that are configured for grasping by hand for hand tightening the hand screws for locking the mounts to the side rails.

20. The table extender of claim 1, wherein at least a portion of each slotted clamp slides between a respective side rail and the platform of the surgical table when the slotted clamps are slid onto the side rails.

21. The table extender of claim 1, wherein the cushion comprises at least one recess for accommodating the optional mounting of the perineal post.

22. The table extender of claim 1, comprising a perineal post configured for optional mounting to the one or more openings of the distal portion.

23. The table extender of claim 1, wherein there is no metal reinforcement extending across a width of the table extender.

\* \* \* \* \*